US008728797B2

(12) United States Patent
Monk et al.

(10) Patent No.: US 8,728,797 B2
(45) Date of Patent: May 20, 2014

(54) YEAST MEMBRANE PROTEIN EXPRESSION SYSTEM AND ITS APPLICATION IN DRUG SCREENING

(75) Inventors: Brian Charles Monk, Dunedin (NZ); Richard David Cannon, Dunedin (NZ); Kenjirou Nakamura, Niigatta (JP); Masakazu Niimi, Tokyo (JP); Kyoko Niimi, Dunedin (NL); Ann Rachel Holmes, Dunedin (NL); Erwin Lamping, Dunedin (NL); David Roger Kay Harding, Palmerston North (NL); Andre Goffeau, Paris (FR); Anabelle Decottignies, London (GB)

(73) Assignee: LA SA Sopartec (BE)

( * ) Notice: Subject to any disclaimer, the term of this patent is extended or adjusted under 35 U.S.C. 154(b) by 1163 days.

(21) Appl. No.: 12/153,902

(22) Filed: May 27, 2008

(65) Prior Publication Data

US 2009/0143308 A1 Jun. 4, 2009

Related U.S. Application Data

(63) Continuation of application No. 10/487,540, filed as application No. PCT/NZ02/00163 on Aug. 23, 2002, now abandoned.

(30) Foreign Application Priority Data

Aug. 24, 2001 (NZ) ........................................ 513755

(51) Int. Cl.
| C12N 1/19 | (2006.01) |
| C12N 15/63 | (2006.01) |
| C12Q 1/68 | (2006.01) |

(52) U.S. Cl.
USPC ..................... 435/254.2; 435/320.1; 435/6.13

(58) Field of Classification Search
None
See application file for complete search history.

(56) References Cited

U.S. PATENT DOCUMENTS

| 5,661,024 A | 8/1997 | Kao et al. ....................... 435/240 |
| 5,876,951 A | 3/1999 | Fowlkes et al. ..................... 435/7 |
| 5,989,832 A | 11/1999 | Trias et al. |
| 6,020,121 A | 2/2000 | Bao et al. |
| 6,103,515 A | 8/2000 | Treichler et al. ............... 435/254 |
| 6,114,310 A | 9/2000 | Chamberland et al. |
| 6,159,705 A | 12/2000 | Trueheart et al. ............... 435/29 |
| 6,187,541 B1 | 2/2001 | Benton et al. |
| 6,214,581 B1 | 4/2001 | Lynch et al. ..................... 435/69 |
| 6,238,873 B1 | 5/2001 | Ames et al. ........................ 435/7 |

FOREIGN PATENT DOCUMENTS

| WO | WO94/23025 | 10/1994 |
| WO | WO99/18211 | 4/1999 |
| WO | WO00/27871 | 5/2000 |
| WO | WO00/77035 | 12/2000 |
| WO | WO02/077035 | 10/2002 |

OTHER PUBLICATIONS

EP Examination Report, Nov. 26, 2007, The University of Otago.
EP Examination Report, Apr. 14, 2009, The University of Otago.
Nakamura, Kenjirou, "Functional expression of *Candida albicans* drug efflux pump Cdr1p in a *Saccharomyces cerevisiae* strain deficient in membrane transports"; vol. 45,No. 12,pp. 3366-3374; Antimicrobial Agents and Chemotherapy, Dec. 2001, American Society for Microbiology.
Marchetti, Oscar, "Potent synergism of the Combination of Fluconazone and Cyclosporine in *Candida albicans*"; Antimicrobial Agents and Chemotherapy, Sep. 2000; p. 2373-2381, vol. 44, No. 9.
Lerner-Marmarosh, Nicole; "Large scale purification of detergent-soluble P-glycoprotein from *Pichia pastoris* cells and characterization of nucleotide binding properties of wild-type, Walker A, Walker B mutant proteins"; The Journal of Biological Chemistry, vol. 274, No. 49, Issue of Dec. 3, pp. 34711-34718, 1999.
Miyazaki, Haruko, "Fluconazone resistance associated with drug efflux and increased transcription of a drug transporter gene, PDH1 in *Candida glabrata* "; Antimicrobial Agents and Chemotherapy, Jul. 1998, pp. 1695-1701, vol. 42, No. 7.
Henry, Karl; "Upregulation of ERG Genes in *Candida* Species by Azoles and other Sterol Biosynthesis Inhibitors"; Antimicrobial Agents and Chemotherapy, Oct. 2000, pp. 2693-2700.
Cannon, Richard D.; "Drug pumping mechanisms in *Candida albicans* "; Jpn.J.Med.Mycol. vol. 39, 73-78, 1998.
Examination Report, Feb. 8, 2011, The University of Otago.
Ball, Maria M., Construction of Efficient Centromeric, Multicopy and Expression Vectors for the Yeast Gluyveromyces marxianus Using Homologous Elements and the Promoter of a Purine-Cytosine-Like Permease; JMMB Research Article, J.Moi.Microbial. Biotechnol (1999) 1(2):347-353; 1999 by Horizon Scientific Press.
David, E Nathaniel, Expression and Purification of the Caccharomyces cerevisiae-a-Factor Receptor (Ste2p), a 7-Transmembrane-segment G Protein-coupled Receptor, The Journal of Biological Chemistry, vol. 272, No. 24, Issue of Jun. 13, pp. 15553-15561, 1997.
Overview of Protein Expression in *Saccharomyces cerevisiae*; Current Protocols in Protein Science (1995) 5.6.1-5.6.7; 2000 by John Wiley & Sons, Inc.
Rogers, Bruce; "The Pleitropic Drug ABC Transporters from *Saccharomyces cerevisiae* "; J.Mol.Microbiol.Biotechnol. (2001) 3(2)207-214.
Decottigniest, Anabelle; "ATPhase and Multidrug Transport Activities of the Overexpressed Yeast ABC Protein Yor1p"; Yeast ABC Transporter Yor1p pp. 12612-12622.
Sanglard, Dominique; "Cloning of *Candida albicans* genes conferring resistance to azole antifungal agents: characterization of CDR2, a new multidrug ABC transporter gene"; Microbiology (1997), 143, 405-415.

(Continued)

Primary Examiner — Michele K Joike
(74) Attorney, Agent, or Firm — Knobbe, Martens, Olson & Bear, LLP

(57) ABSTRACT

The invention relates to an in vitro cell based expression system for overexpressing heterologous pump proteins associated with drug resistance into the membrane of the host cell for drug screening applications.

25 Claims, 17 Drawing Sheets

(56) References Cited

OTHER PUBLICATIONS

Ben-Yaacov, Rina; "*Candida albicans* gene encoding resistance to benomyl and methotrexate is a multidrug resistance gene"; Antimicrobial Agents and Chemotherapy, Apr. 1994, p. 648-652.

Lai, M.H., "Nucleotide sequence of cytochrome p450 (lanosterol 14a-demethylase) from *Candida albicans*"; Nucleic Acids Research, vol. 17, No. 2, (1989); pp. 167-186.

Sanglard, Dominique; "Multiple resistance mechanisms to azole antifungals in yeast clinical isolates"; Drug Resistance Updates (1998), 255-265.

Niimi, K., "Chemosensitizaiton of Fluconazole Resistance in *Saccharamyces cerevisiae* and Pathogenic Fungi by a D-Octapeptide Derivative"; Antimicrobial Agents and Chemotherapy, Apr. 2004, p. 1256-1271.

Lamb, David C.; "The Mutation T315A in *Candida albicans* Sterol 14a-Demethylase causes reduced enzyme activity and fluconazole resistance through reduced affinity"; The Journal of Biological Chemistry, vol. 272, No. 9, Issue of Feb. 28, pp. 5682-5688, 1997.

Sandlard, Dominique; "Role of ATP-Binding-Cassette Transporter Genes in High-Frequency Acquisition of Resistance to Azole Antifungals in *Candida glabrata* "; Antimicrobial Agent and Chemotherapy, Apr. 2001, p. 1174-1183.

Prasad, Rajendra, "Molecular cloning and characterization of a novel gene of *Candida albicans*, CDR1, conferring multiple resistance to drugs and antifungals"; CurrGenet (1995), 27: 320-329.

Alban De Kerchove d'Exaerde; Functional Complementation of Null Mutation of the Yeast *Saccharomyces cerevisiae* Plasma Membrane H+-ATPase by a Plant H+-ATPase Gene; The Journal of Biological Chemistry 1995 by The American Society for Biochemistry and Molecular Biology, Inc.; vol. 270, No. 40, Issue of Oct. 6, pp. 23828-23837.

Balzi, Elisabetta, Genetics and biochemistry of yeast multidrug resistance, BBA Biochimica at Biophysics Acta; 1994 Elsevier B.V., 1187(1994)152-162.

Luo, Hong, The Two Major Types of Plant Plasma Membrane H+-ATPase Show Different Enzymatic Properties and Confer Differential pH Sensitivity of Yeast Growth; Plant Physiology, Feb. 1999, vol. 119, pp. 627-634, 1999 The American Society of Plant Physiologists.

Ambesi, Anthony, Isolation of Transport-Competent Secretory Vesicles from *Saccharomyces cerevisiae*; Analytical Biochemistry 251, 127-129 (1997) Article No. AB972257; The Academic Press.

Lynn Helena Caporale, Chemical Ecology: A view from the pharmaceutical industry; Proc.Natl.Acad.Sci. USA; vol. 92, pp. 75-82, Jan. 1995.

Marcin Lolaczkowski, In vivo Characterization of the drug resistance profile of the major ABC Transporters and other components of the yeast pleiotropic drug resistance network; Microbial Drug Resistance; vol. 4, No. 3, 1998; Mary Ann Liebert, Inc.

Mao Scarborough, Purification of functional human P-glycoprotein expressed in *Saccharomyces cerevisiae*; Biochim Biophys Acta Jul. 5, 1997; 1327(1):107-18.

Huang P., Functional expression of the cystic fibrosis transmembrane conductance regulator in yeast; Biochim Biophys Acta May 22, 1996;1281(1):8090.

Bayer Ag; Towards 3D structures of G protein-coupled receptors: a multidisciplinary approach; Curr Med Chem Sep. 7, 2000;(9):861-88.

Mahanty, SK; High yield expression of the neurospora crasse plasma membrane H (+)-ATPase in *Saccharomyces cerevisiae*; J Biol Chem Jul. 1, 1994;269(26):17705-12.

Balzi, Elisabetta; Yeast Multidrug Resistance: The PDR Network; Journal of Bioenergetics and Biomembranes, vol. 27, No. 1, 1995.

JL Brodsky, Protein Expression in sec6 Vesicles; J. Cell. Biol.120, 95 (1993) 168-185.

Miyazaki, Haruko, Fluconazone resistance associated with drug efflux and increased transcription of a drug transporter gene, PDH1, in *Candida glabrata*; Antimicrobial Agents and Chemotherapy, Jul. 1998, p. 1695-1701; American Society for Microbiology.

Cannon, Drug Pumping Mechanisms in *Candida albicans*; Jpn.J. Med.Mycol. vol. 39, 73-78, 1998.

Decottigniest, Althea, ATPase and Multidrug Transport Activities of the Overexpressed Yeast ABC Protein Yor1p, 1998.

Decottigniest, Anabelle; ATPase and Multidrug Transport Activities of the Overexpressed Yeast ABC Protein Yor1p; Unite de Biochimie Physiologique, Universite Catholique de Louvain, 1998.

Canton, Richard D.; Drug Pumping Mechanisms in *Candida albicans*; Jpn.J.Med.Mycol., vol. 39; 75-78 1996.

Leppert, Gregory; Cloning by gene amplification of two loci conferring multiple drug resistance *Saccharomyces*; 1998 by The Genetics Society of America; Genetics 125:13-20 (May 1990).

Rogers, Bruce; The Pleitripic Drug ABC Transporters from *Saccharomyces cerevisiae*; 2001 Horizon Scientific Press; J. Moi. Microbiol. Biotechnol. (2001), 3(2):207-214.

Marchetti, Oscar; Potent Synergism of the Combination of Fluconazole and Cylcosporine in *Candida albicans*; Antimicrobial Agents and Chemotherapy, Sep. 2000 p. 2373-2381; 2000, The American Society of Microbiology.

Sanglard, Dominique; Role of ATP-Binding-Cassette Transporter Genes in High-Frequency Acquisition of Resistance to Azole Antifungals in *Candida glabrata*; Antimicrobial Agents and Chemotherapy, Apr. 2001, p. 1174-1183; (2001) The American Society for Microbiology.

Henry, Karl, Upregulation of ERG Genes in *Candida* Species by Azoles and Other Sterol Biosynthesis Inhibitors; Antimicrobial Agents and Chemotherapy, Oct. 2000, p. 2693-2700; The American Society for Microbiology.

Lerner-Marmarosh, Nicole, Large Scale Purification of Detergent-soluble P-glycoprotein from *Pichia pastoris* Cells and Characterization of Nucleotide Binding Properties of Wild type, Walker A, Walker B Mutant Proteins; The Journal of Biological Chemistry; 1999 by the American Society for Biochemistry and Molecular Biology, Inc.; vol. 274, No. 49, Issue of Dec. 3, pp. 34711-34718, 1999.

Nakamura, Kenjirou, Functional Expression of *Candida albicans* Drug Efflux Pump Cdr1p in a *Saccharomyces cerevisiae* Strain Deficient in Membrane Transporters; Antimicrobial Agents and Chemotherapy, Dec. 2001, p. 3366-3374; American Society for Microbiology.

North, Alan, Molecular Physiology of P2X Receptors; 2002, The American Physiological Society; 82: 1013-1067, 2002.

Sanglard, Dominique; The ATP Binding Cassette Transporter Gene CgCDR1 from *Candida glabrata* is involved in the resistance of clinical isolates to azole antifungal agents; Antimicrobial Agents and Chemotherapy, Nov. 1999, p. 2753-2765; 1999 The American Society for Microbiology.

Translation of Notice of Reasons for Rejection, dated Aug. 11, 2008, Patent Application No. 2003-523664.

Nakamoto et al, The Journal of Biological Chemistry, vol. 266, No. 12, 1991, pp. 7940-7949, Expression of the Yeast Plasma. . . .

Laizéet al, FEBS Letters 373, 1995, pp. 269-274, Functional expression of the human CHIP28 water channel in a yeast. . . .

Cannon et al, JPN. J. MED. MYCOL., vol. 39, 1998, pp. 73-78, Drug Pumping Mechanisms in *Candida albicans*.

Albertson et al, Antimicrobial Agents & Chemotherapy, vol. 40, No. 12, Dec. 1996, pp. 2835-2841, Multiple Efflux Mechanisms. . . . .

Balzi et al, The Journal of Biological Chemistry, vol. 269, No. 3, 1994, pp. 2206-2214, PDR5, a Novel Yeast Multidrug. . . .

Belliet al, Yeast 14, 1998, pp. 1127-1138, Functional Analysis of Yeast Essential Genes Using a Promoter-Substitution. . . .

Boeke et al, MOL GEN GENET 197, 1984, pp. 345-346, A positive selection for mutants lacking orotidine-5'-phosphate. . . .

Bradford, Analytical Biochemistry 72, 1976, pp. 248-254, A Rapid and Sensitive Method for the Quantitation of Microgram. . . .

Cannon et al, Journal of Bacteriology, May 1994, pp. 2640-2647, Molecular Cloning and Expression of the *Candida albicans* . . . .

Carvajal et al, MOL GEN GENET 256, 1997, pp. 406-415, Molecular and phenotypic characterization of yeast PDR1 mutants that. . . .

Clark et al, Antimicronial Agents & Chemotherapy, vol. 40, No. 2 1996, pp. 419-425, Correlation between Rhodamine 123. . . .

Decottignies et al, Nature Genetics, vol. 15, 1997, pp. 137-145 Complete inventory of the yeast ABC proteins.

(56) References Cited

OTHER PUBLICATIONS

Decottignies et al, The Journal of Biological Chemistry, vol. 273 No. 20, 1998, pp. 12612-12632, ATPase and Multidrug....

Decottignies et al, The Journal of Biological Chemistry, vol. 269 No. 17, 1994, pp. 12797-12803, Solubilization and....

Fling et al, Mol Gen GENET 227, 1991, pp. 318-329, Analysis of a *Candida albicans* gene that encodes a novel mechanism for....

Goffeau et al, Methods in Enzymology, vol. 157, 1988, pp. 528-533, Plasma Membrane ATPase from the Yeast *Saccharmyces*....

Huang et al, Biochimica et Biophysica Acta 1281, 1996, pp. 80-90, Functional expression of the cystic fibrosis....

Kerchove d'Exaerde et al, The Journal of Biological Chemistry, vol. 270, No. 40, 1995, pp. 23828-23837, Functional....

Kolaczkowski et al, The Journal of Biological Chemistry, vol. 271 No. 49, 1996, pp. 31543-31548, Anticancer Drugs, Ionophoric....

Krishnamurthy et al, Yeast, vol. 14, 1998, pp. 535-550, De-letion of Transmembrane Domain 12 of CDR1, a Multidrug....

Krishnamurthy et al, FEMS Microbiology Letters 158, 1998, pp. 69-74, Characterisation of human steroid hormone transport....

Luo et al, Plant Physiology, vol. 119, Feb. 1999, pp. 627-634, The Two Major Types of Plant Plasma membrane H +-ATPases Show....

Maesaki et al, Journal of Antimicronial Chemotherapy 44, 1999, pp. 27-31, Rhodamine 6G efflux for the detection of CDR1-....

Mahanty et al, The Journal of Biological Chemistry, vol. 269, No. 26, 1994, pp. 17705-17712, High Yield Expression of the....

Mao et al, Biochemica et Biophysica Acta 1327, 1997, pp. 107-118, Purification of functional human P-glycoprotein expressed....

Marchetti et al, Antimicrobial Agents & Chemotherapy, vol. 44, No. 11, Nov. 2000, pp. 2932-2938, Fluconazole plus....

Marchetti et al, Antimicrobial Agents & Chemotherapy, vol. 44, No. 9, Sep. 2000, Potent Synergism of the Combination of....

Mitchell et al, J. Peptide Res. 56, 2000, pp. 318-325, Poly-arginine eneters cells more efficiently than other ploycatonic....

Miyazaki et al, Antimicrobial Agents & Chemotherapy, vol. 42, No. 7, Jul. 1998, pp. 1695-1701, Fluconazole Resistance....

Monk et al, Journal of Bacteriology, vol. 173, No. 21, Nov. 1991, pp. 6826-6836, Cloning and Characterization of the Plasma....

Nakayama et al, Microbiology 144, 1998, pp. 2407-2415, A controllable gene-expression system for the pathogenic funguas....

Potenza et al, Yeast, vol. 8, 1992, pp. 549-558, SEC6 Encodes an 85 kDa Soluable Protein Required for Exocutosis in Yeast.

Prasad et al, Curr Genet 27, pp. 320-329, Molecular cloning and characterization of a nobel gene of *Candida*....

Sanglard et al, Antimicrobial Agents & Chemotherapy, vol. 40, No. 10, Oct. 1996, pp. 2300-2305, Susceptibilities of *Candida*....

Sanglard et al, Microbiology 143, 1997, pp. 405-416, Cloning of *Candida albicans* genes conferring resistance to azole....

Sanglard et al, Antimicrobial Agents & Chemotherapy, vol. 39, No. 11, Nov. 1995, pp. 2378-2386, Mechanisms of Resistance....

Scherer et al, Journal of Clinical Microbiology, vol. 25, No. 4, pp. 675-679, Application of DNA Typing Methods to ... 1987.

Seto-Young et al, The Journal of Biological Chemistry, vol. 269, No. 39, 1994, pp. 23988-23995, Mutational Analysis of the....

Schwartz et al, Annals New York Academy of Sciences, 1982, pp. 253-271, Mechanism of Action of Digitalis: Is the Na, K-ATPase....

White et al, Antimicrobial Agents & Chemotherapy, vol. 41, No. 7 Increased mRNA Levels of *ERG16, CDR*, and *MDR1* Correlate with....

White et al, Clinical Microbiology Reviews, vol. 11, No. 2, Apr. 1998, pp. 382-402, Clinical, Cellular, and Molecular Factors....

Wilson et al, Yeast 16, 2000, pp. 65-70, A recyclable *Candida albicans* URA3 cassette for PCR product-directed gene disruptions.

Calabrese et al, Microbiology 146, 2000, pp. 2743-2457, A novel multidrug efflux transporter gene of the major facilitator....

Milewski et al, Antimicrobial & Chemotherapy, vol. 45, No. 1, Jan 2001, pp. 223-228, Unusual Susceptibility of a Multi-....

Moran et al, Antimicrobial Agents & Chemotherapy, vol. 42, No. 7, Jul. 1998, pp. 1819-1830, Indentification and Expression of....

Sanglard et al, Antimicrobial Agents & Chemotherapy, vol. 43, No. 11, Nov. 1999, pp. 2753-2765, The ATP Binding Cassette....

Talibi et al, Journal of Bacteriology, vol. 181, No. 1, Jan. 1999 pp. 231-240, Isolation of a Putative *Candida albicans*....

Gupta et al, FEBS Letters 481, 2000, pp. 77-80, Heterologous expression of a mammalian epithelial sodium channel in yeast.

Kiser et al, Archives of Biochemistry & Biophysics, vol. 390, No. 2, 2001, pp. 195-205, Expression and Degradation of the....

Katzmann et al., "Transcriptional Control of the Yeast PDR5 Gene by the PDR3 Gene Product," Molecular and Cell Biology, Jul. 1994, vol. 14 (7), pp. 4653-4661.

YEAST MEMBRANE PROTEIN EXPRESSION SYSTEM AND ITS APPLICATION IN DRUG SCREENING

CLAIM OF PRIORITY

This is a continuation of U.S. patent application Ser. No. 10/487,540, filed Sep. 16, 2004, now abandoned which is a nationalization of PCT/NZ02/00163, filed Aug. 23, 2002, which claims priority to New Zealand provisional patent application No. 513,755 and published in English. Each of these applications is herein incorporated fully by reference.

FIELD OF THE INVENTION

This invention relates to a protein expression system, particularly although by no means exclusively, to a plasma membrane protein expression system, and the application of this system in understanding the basic biology of membrane bound proteins and in drug discovery.

BACKGROUND

Proteins located in the plasma membrane or surface membranes of target cells are amongst the most prominent, accessible and attractive sites for intervention with small molecule drugs for pharmaceutical and agrochemical purposes. For example, drugs such as ouabain and the cardiac glycosides are effective therapeutics in the treatment of heart disease because of their activity against isoforms of the membrane protein $Na^+, K^+$-ATPase of mammalian cells (Schwartz A, et al, 1982).

Individual membrane proteins of interest that are located at the cell surface may be constitutively expressed cellular components found in a host or a pathogenic organism. Alternatively, the expression of these proteins may also be affected by mutation or by interactions between such cells and other organisms. These membrane proteins include transporters, channels, receptors and enzymes plus proteins with structural, regulatory or unknown roles. Various members of these classes of proteins are known to affect the growth, viability, and functional capacity of host organisms, tissues or cells. In particular, several classes of membrane proteins are known to be involved in drug resistance. These include the drug efflux pump proteins which act to increase the efflux of particular drugs, such as antibiotics and other xenobiotics, from the inside of a cell to the outside. This activity lowers the concentration of the drug at the intracellular target site to levels which are no longer effective. Yeast cell expression systems for testing drugs that inhibit drug efflux pump proteins are known. Decottignies et al 1998 describes a number of strains of *Saccharomyces cerevisiae* in which varying endogenous drug efflux pump proteins (ABC transporter proteins) have been deleted and a further endogenous membrane protein overexpressed in the cell membrane. Such a system also employs the use of regulators which aid in this overexpression. Examples of such regulators are described in Carjaval et al (1997). However, such a system is restrictive in its application as it may be species specific, ie it may only identify potential drugs useful in inhibiting drug resistance in *Saccharomyces cerevisiae*.

As the problem of drug resistance is widely found in all fauna and flora, and not just in yeast, there exists a need to develop a simple in vitro cell based membrane protein expression system for testing potential inhibitors of drug efflux pump proteins, as well as other membrane proteins associated with drug resistance, from different species.

In addition, as the number of potential test compounds, located mainly in compound libraries, is increasing in both size and complexity, there is a need for such a simple in vitro, cell based membrane protein expression system to screen for agonists or antagonists of putative membrane protein drug targets from a broad range of species and which can be adapted for high throughput formats.

It is an object of the present invention to go some way towards providing for these needs and/or to provide the public with a useful choice.

SUMMARY OF INVENTION

The present invention provides a protein expression system comprising:
i) a host yeast cell comprising a mutant strain deficient in one or more naturally occurring drug efflux pump proteins; and
ii) a vector comprising the coding sequence of a target heterologous membrane protein, said sequence being under the control of a promoter which, upon transformation of said host cell and chromosomal integration, causes over-expression of the functional target protein in the membrane of the host cell, wherein said functional target protein is expressed prominently in the membrane of the host cell and is accessible for drug screening applications.

The host yeast cell may comprise a strain of the genus *Saccharomyces*.

The preferred yeast strain is *Saccharomyces cerevisiae* AD1-8u⁻.

In some applications, the host cell may contain a mutation that leads to the formation of secretory vesicles whose ability to fuse normally with the plasma membrane is temperature sensitive. A preferred mutated strain is the sec6-4 mutant of the AD1-8u⁻ strain.

The coding sequence of the target heterologous protein may be incorporated into the host cell in a defined location in the genome such as downstream of an endogenous promoter.

The coding sequence of the target heterologous membrane protein may comprise the entire natural coding sequence of the target protein, or a functional fragment or variant thereof which, upon transformation and expression, will produce a functional membrane protein with a detectable phenotype.

The target heterologous membrane protein of the invention may comprise a drug efflux pump protein such as those involved in multidrug resistance in fungi, but may also include other molecules such as the P-glycoprotein, the cystic fibrosis transmembrane conductance regulator and other human, animal, plant and microbial plasma membrane proteins that play a role in the conferral of resistance or sensitivity to xenobiotics, the etiology of disease or the modulation of physiology, growth and development.

Preferably, the target membrane protein is a drug efflux pump protein and the candidate compound is an efflux pump inhibitor.

The vector used to integrate the coding sequence of the target heterologous membrane protein is preferably a plasmid vector which contains elements which allow replication in *E. coli*. The vector may also include a transcription terminator that is functional in the host cell. In addition, the vector may include a marker that confers a selectable phenotype on the cells after transformation. The promoter is selected from the group of promoters comprising constitutive *S. cerevisiae* PDR5 and PAM1 promoters, copper controllable CTR3, glucose inducible ADH1 and PGK promoters, the galactose inducible GAL promoter, the doxycycline controllable bacterial tet0 promoter and the tet0::ScHOP1 controllable cassette. The preferred promoter is PDR5. The preferred vector is pABC3.

The yeast host strain may further comprise a mutated transcriptional regulator coding sequence that causes overexpression of the target coding sequence leading to abundant expression of the target protein in the membrane of the host cell. The mutated transcriptional mutator may be Pdr1-3p.

The present invention further provides a method of screening for drugs useful as a pharmaceutical or agrochemical comprising the steps of:
i) transforming the chromosomal DNA of a host yeast cell, comprising a mutant strain deficient in one or more naturally occurring drug efflux pump proteins, with DNA comprising the coding sequence of a target heterologous membrane protein, said sequence being under the control of a host promoter leading to over-expression of the functional target protein in the membrane of the host cell, wherein said functional target protein is expressed prominently in the membrane of the host cell and is accessible for drug screening applications;
ii) introducing at least one candidate compound to said host cell environment or the environment of a plasma membrane fraction derived from the transformed host strain; and
iii) measuring the effect, if any, of the candidate compound on the host cell growth and/or viability and/or specific biochemical or physiological functions mediated by the target membrane protein; and/or measuring the binding of the candidate compound to the target membrane protein.

The target heterologous membrane protein of the invention may comprise a drug efflux pump protein such as those involved in multidrug resistance in fungi, but may also include other molecules such as the P-glycoprotein, the cystic fibrosis transmembrane conductance regulator and other human, animal, plant and microbial plasma membrane proteins that play a role in the conferral of resistance or sensitivity to xenobiotics, the etiology of disease or the modulation of physiology, growth and development.

Preferably, the target membrane protein is a drug efflux pump protein and the candidate compound is an efflux pump inhibitor.

Preferably, the host yeast cell is of the genus *Saccharomyces*, and most preferably the host cell is a *Saccharomyces* cell which has been genetically altered to be depleted in one or more natural membrane proteins. A suitable host cell is the *Saccharomyces cerevisiae* AD1-8u⁻ strain. In another embodiment a suitable host cell may be a sec6-4 mutant of the AD1-8u⁻ strain. In a further embodiment the host strain may be a derivative of the AD1-8u⁻ strain modified to select for a novel phenotype, such as prototrophy, an auxotrophic requirement or drug sensitivity.

A transformation cassette derived from a plasmid vector may be used to transform the chromosomal DNA of the host cell. The vector may contain elements which allow replication in *Escherichia coli*, plus a promoter such as a *Saccharomyces cerevisiae* promoter and more preferably the PDR5 promoter. Activity of the *Saccharomyces* promoter is preferably under the additional control of a mutated transcriptional regulator causing over-expression of the target coding sequence, leading to abnormal expression of the target protein in the membrane of the host cell. The mutated transcriptional regulator Pdr1-3p is preferred and is located in the genome of the host cell. In some applications, a transcriptional terminator that is functional in yeast may be included in the vector. Either the natural terminator of the gene encoding the membrane protein or the yeast PGK1 terminator is preferred. In other applications immunological, affinity or fluorescent tags may be included in the vector. In some further applications, a selectable marker may also be included in the vector such as *S. cerevisiae* URA3 marker. In other applications a *S. cerevisiae* centromere or autonomously replicating sequence might be included in the vector. The vector is preferably pABC3.

Compounds which are identified as useful bioactives, pharmaceuticals or agrochemicals using the method and system of the invention also form part of the present invention. These may include compounds obtained from compound libraries, such as NK20 as defined below.

The method and system of the present invention may also find application for the over-expression of yeast and heterologous target membrane proteins for the purposes of physiological study, biochemical analysis, enzyme purification and structural analysis of said target membrane proteins. Purified membrane proteins produced by the method and system of the invention also form part of the present invention.

In a further embodiment, the present invention provides a kit for screening for drugs useful as a pharmaceutical or agrochemical comprising the protein expression system of the present invention together with suitable instructions.

In a further form of the invention the target membrane protein may be required for viability or virulence of a pathogen or the progression of a disease. For example, the target protein may be required for the attachment or uptake of viruses or other pathogens. In such cases, the effect, if any, of a compound on the function of the target membrane protein may be measured.

Although the invention is broadly as defined above, it is not limited thereto and also includes embodiments of which the following description provides non-limiting examples.

BRIEF DESCRIPTION OF THE DRAWINGS

The present invention will now be described with reference to the figures of the accompanying drawings in which.

Figure 6:
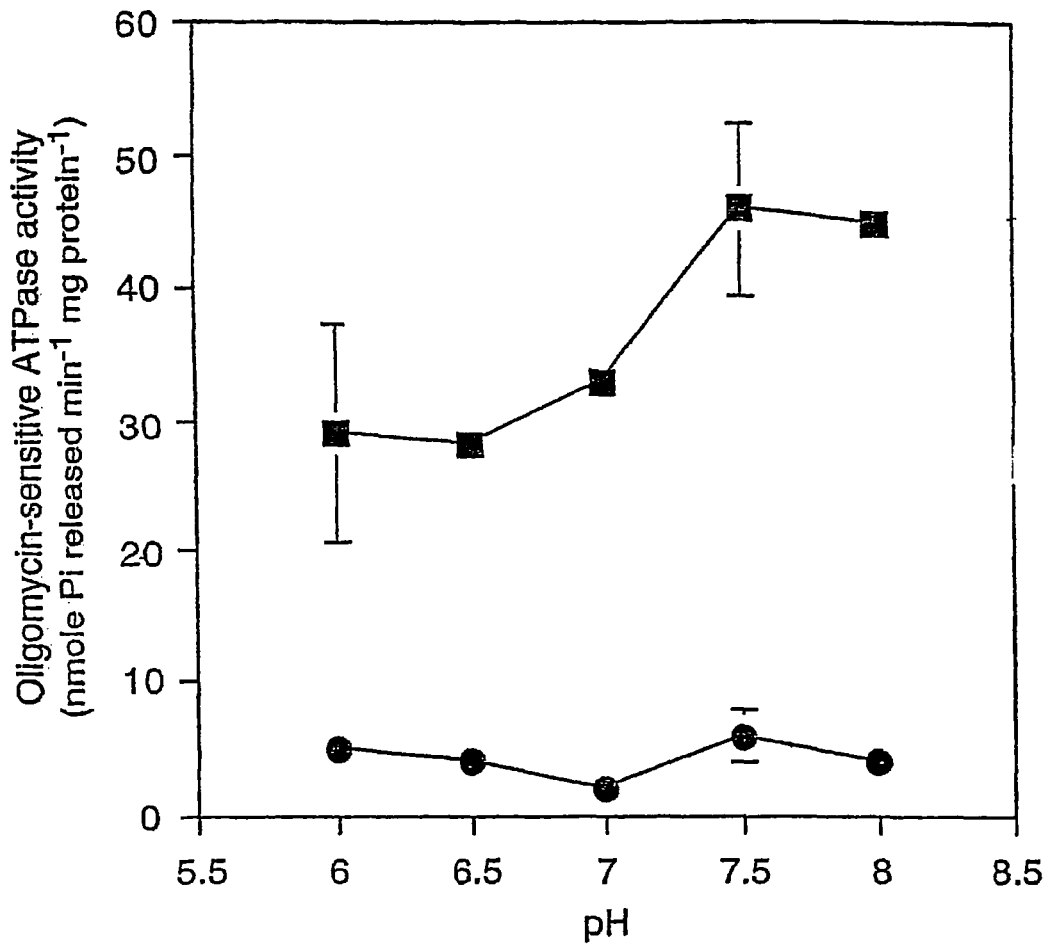

FIG. 6. shows oligomycin-sensitive C. albicans Cdr1p-ATPase activity in plasma membrane fractions. Membrane fractions were isolated from S. cerevisiae AD1002 (■) or parental AD1-8u⁻ cells (●). ATPase assays were carried out at 30° C. for 30 min, as described in Materials and methods for Example 2. The oligomycin-sensitive activity was determined as the difference in ATPase activity in the presence and absence of 20 µM oligomycin. The ATPase activity was completely sensitive to vanadate (100 µM) and insensitive to aurovertin B (20 µM). The results are the means (+/−SD) of four determinations carried out on two membrane preparations.

Figure 7:
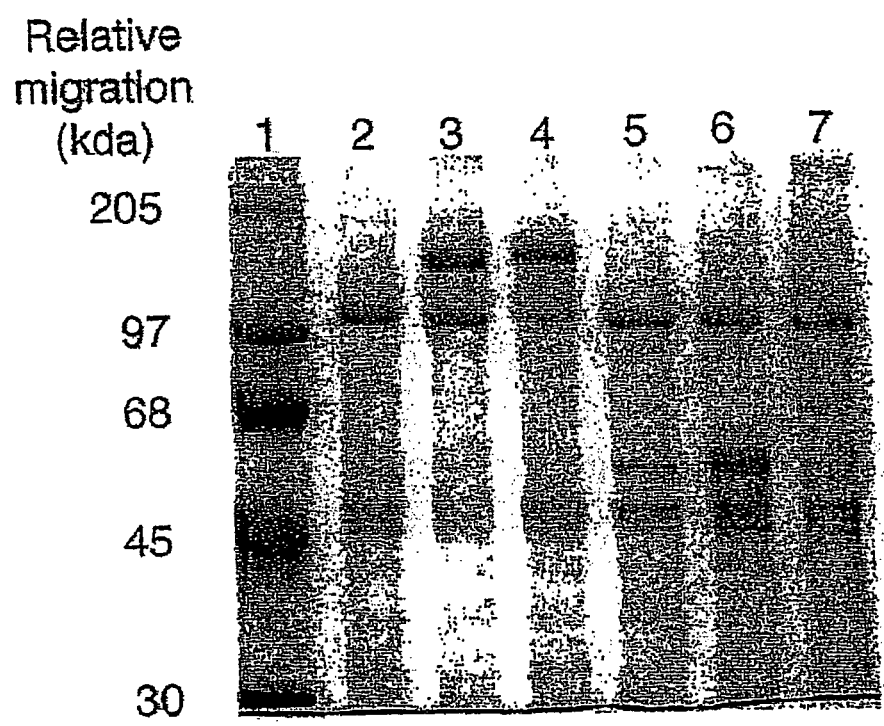

FIG. 7 shows the protein profiles of plasma membrane proteins obtained from control strains AD1-8u⁻, AD-pABC, and derivative strains AD-PDR5, AD-CDR1, AD-BEN$^R$ and AD-ERG11. Samples of 30 µg of SDS solubilised protein were separated in an 8% polyacrylamide gel and stained with Coomassie blue. Lane 1 shows the relative migration of molecular weight markers. Plasma membranes were obtained from strains AD-pABC (lane 2), AD-PDR5 (lane 3), AD-CDR1 (lane 4). AD-ERG11 (lane 5), AD-BEN$^R$ (lane 6) and AD1-8u⁻ (lane 7).

Figure 8:
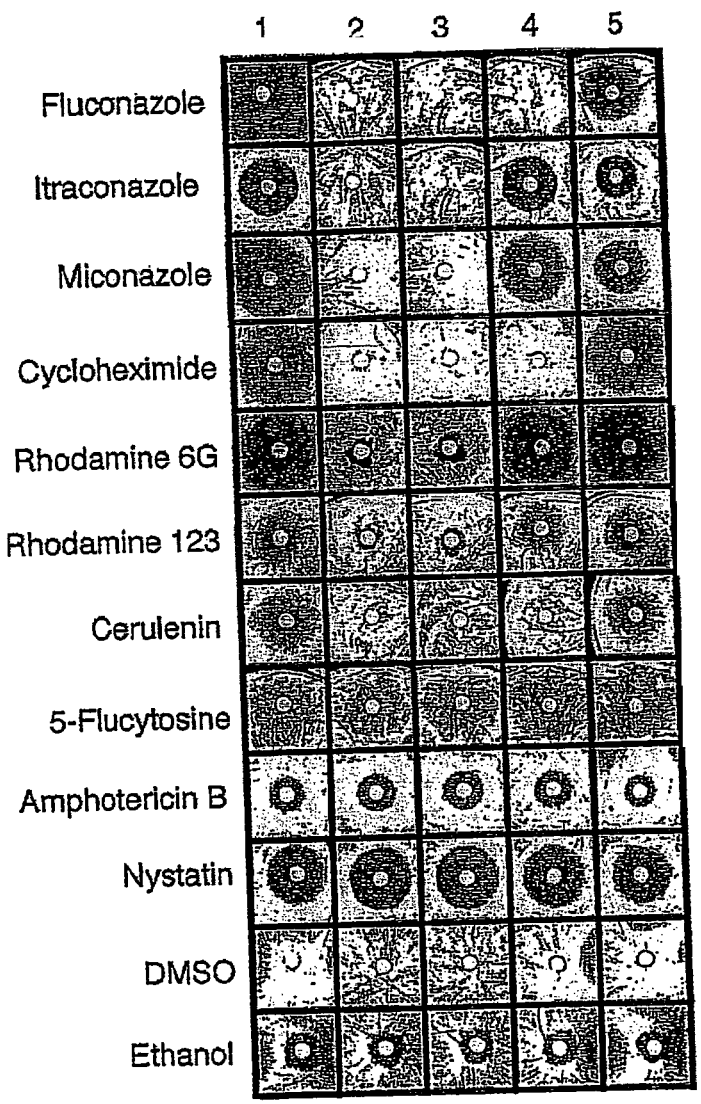

FIG. 8 shows the sensitivity of a control S. cerevisiae strain (AD-pABC, column 1) and strains expressing Pdr5p (AD-PDR5, column 2), Cdr1p (AD-CDR1, column 3), Ben$^R$p (AD-BENR, column 4) and Erg11p (AD-ERG11, column 5), to various antifungal drugs and chemicals. The cells were spread on CSM-agar plates and exposed to the drugs or chemicals applied to filter disks and incubated at 30° C. for 48 h. The amounts of individual drugs are given in the Materials and Methods section of Example 3. Rhodamine 6G and rhodamine 123 were dissolved in ethanol and the other antifungals were dissolved in DMSO.

Figure 9:
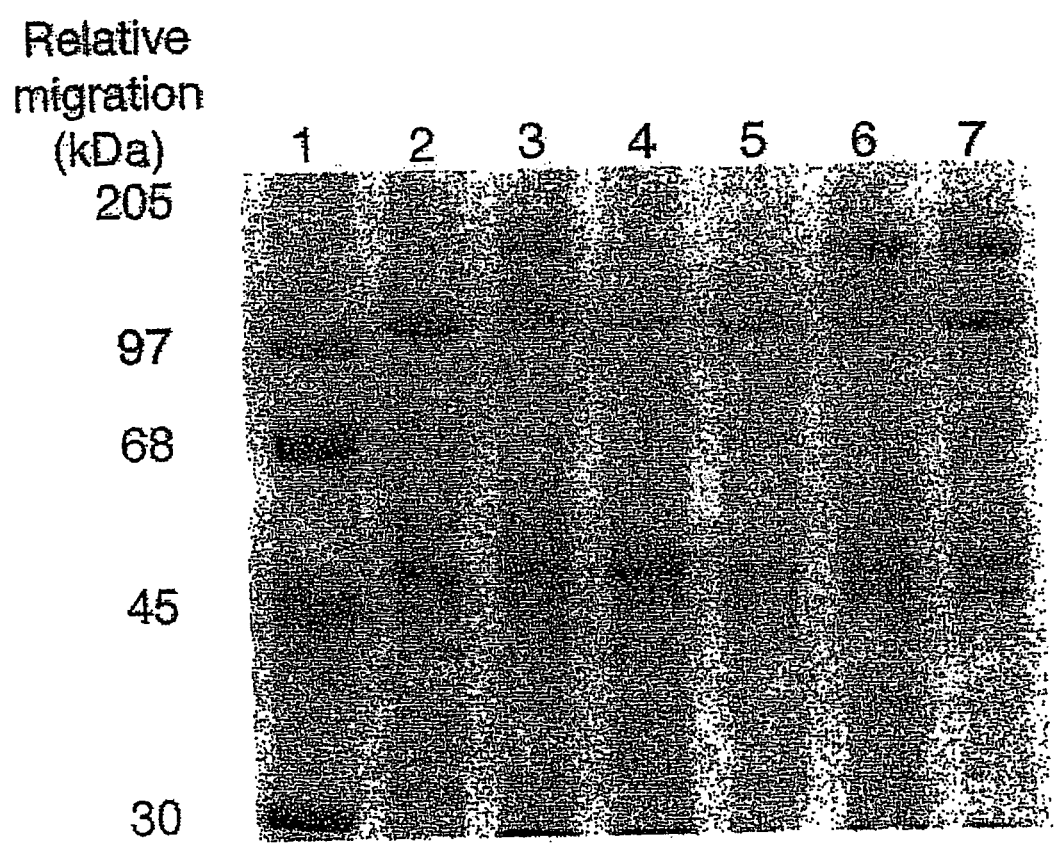

FIG. 9 shows the effect on the expression of Pdr5p in the AD1-8u-background by an SfiI locus located at nucleotides −30 to −18 and a PacI locus located at nucleotides −11 to −4 relative to the PDR5 start codon. Plasma membrane proteins (30 µg) separated through 8% polyacrylamide gel were stained with Coomassie blue. Lane 1 shows the relative migration of molecular weight markers. Plasma membranes were obtained from strains AD1-8u- (lane 2), AD-PDR5 (lane 3), AD-PDR5-SfiI/PacI (lane 4). AD-PDR5-SfiI (lane 5), AD-PDR5-PacI (lane 6) and AD1234567 (lane 7).

FIG. 10. shows the in vitro characterisation of the Pdr5p inhibitor KN20. (A) Inhibition profiles of oligomycin-sensitive Pdr5p ATPase activity by the purified peptides D-NH$_2$-asparagine-tryptophan-tryptophan-lysine-valine-arginine-arginine-arginine-CONH$_2$ (KN0) and its singly substituted Mtr-derivative KN20. (B) Inhibition profile with KN20 on the oligomycin-sensitive Cdr1p ATPase activity of plasma membranes from AD1002 minus the oligomycin-sensitive ATPase activity of plasma membranes from the isogenic AD1-8u⁻ strain.

FIG. 11. shows assays which measure the chemosensitisation of AD124567 cells to fluconazole by the lead compound KN20. (A) Checkerboard drug susceptibility assay of AD124567 in the presence of the indicated concentrations of fluconazole and KN20. (B) Disk drug susceptibility assay of AD124567. This assay was conducted, as described in Materials and methods for example 4, in the absence or presence of fluconazole (120 µg/ml), and in the presence of (1) KN0 (47 nanomole), (2) KN20 (47 nanomole) or (0) control amounts of DMSO applied to disks FIG. 12. shows assays which measure the chemosensitisation of AD1002 and ATCC 10261 cells to fluconazole by lead compound KN20. (A) Checkerboard drug susceptibility assay of AD1002. This assay was conducted as described in Materials and methods in the presence of the indicated concentrations of fluconazole and KN20. (B) Disk drug susceptibility assay of AD1002. This assay was conducted, as described in Materials and methods for Example 4, in the absence or presence of 5 µg/ml fluconazole, with (1) KN0 (12 nanomole), (2) KN20 (12 nanomole) or (0) control amounts of DMSO applied to the disks. (C) Checkerboard drug susceptibility assay of ATCC 10261. This assay was conducted, as described in Material and methods for Example 4, in the presence of the indicated concentrations of fluconazole and KN20. D indicates cell death as measured by a failure to recover any colony forming units when samples from microtitre plate wells were cultured on solid YPD medium.

FIG. 13 shows checkerboard drug susceptibility assays of strains (a) AD-BEN$^R$ and (B) AD-ERG11. The assays were conducted, as described in Materials and methods for Example 4, in the presence of the indicated concentrations of fluconazole and KN20. D indicates cell death as measured by a failure to recover any colony forming units when samples from microtitre plate wells were cultured on solid YPD medium.

Figure 14:
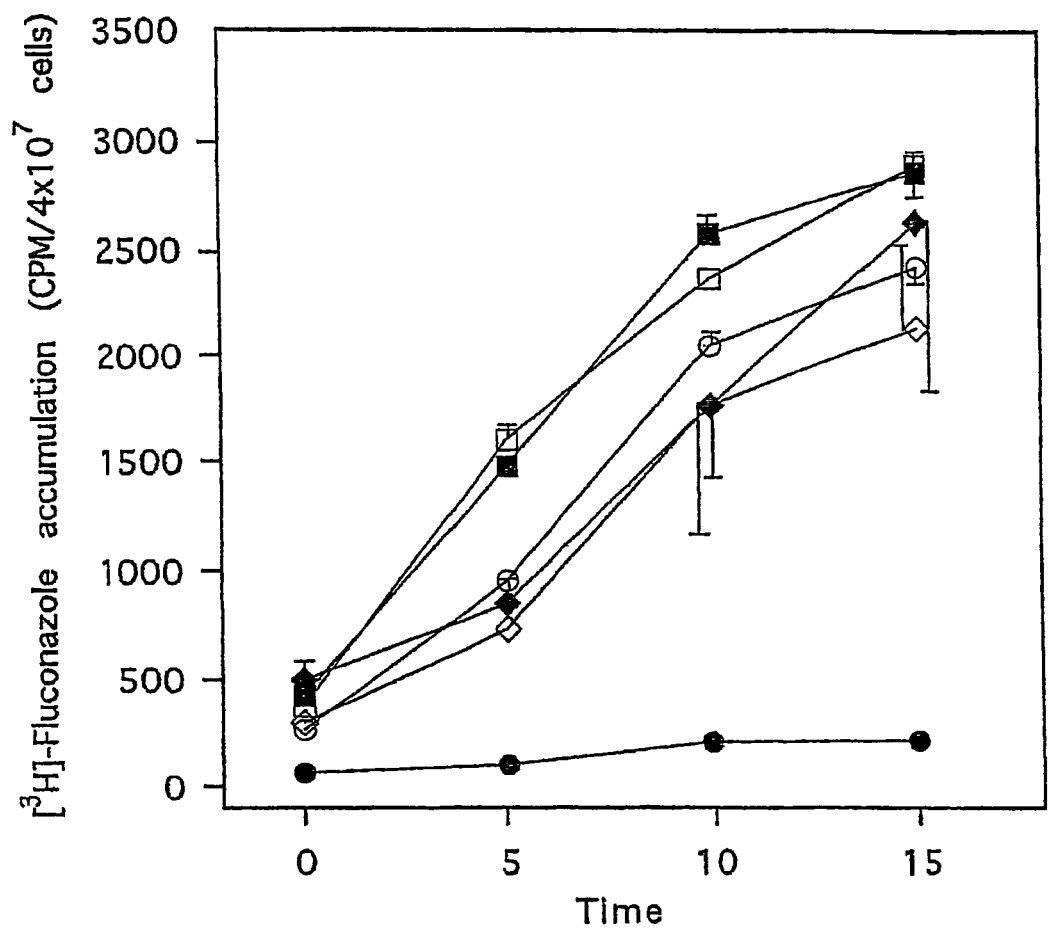

FIG. 14. shows azide-dependent fluconazole accumulation by S. cerevisiae AD1002. [$^3$H]Fluconazole accumulation was measured in the presence (open symbols) or absence (closed symbols) of sodium azide (20 mM). Strains used: AD1-8u⁻ (■,□); AD1-8u⁻/pSK-PDR5PPUS (♦,◊) AD1002 (●, ○). Results are the means±SD of six separate determinations on two batches of cells.

FIG. 15. shows energy-dependent rhodamine 6G efflux from strains AD124567, AD1-8u⁻ and AD1002. De-energised cells were pre-loaded with rhodamine 6G, as described in Materials and methods for Example 4. The efflux of rhodamine 6G at 30° C. was followed by direct measurement of fluorescence in cell supernatants following glucose (2 mM) addition to cell suspensions. (A) The kinetics of energy-dependent rhodamine 6G efflux in strains AD1002 (■) and AD1-8u⁻ (●). The fluorescence in supernatants of AD1002 cells in the absence of added glucose is also shown (○). (B) The effect of KN20 concentration on the energy-dependent efflux of rhodamine 6G from AD124567 cells. The indicated concentrations of KN20 were added to AD124567 cells pre-loaded with rhodamine 6G, the cells were preincubated for 5 minutes at 30° C. and glucose added to commence rhodamine efflux.

DETAILED DESCRIPTION OF PREFERRED EMBODIMENTS OF THE INVENTION

The present invention primarily relates to a method of screening potentially useful drugs for animal, human and plant applications essentially using a system which involves the genetic construction of plasmid vectors that, upon transformation of a suitable host, enable the heterologous overexpression, analysis and application of fully functioning cell surface target membrane proteins. Preferred target membrane proteins are those involved in multidrug efflux, and preferred host cells include laboratory strains of yeast that are preferably also depleted in endogenous membrane transporters that may carry out similar functions. However, this method may also be useful for screening drugs whereby the target is a protein or enzyme which carries out a cellular function that can lead to drug resistance or some other detectable phenotype when expression of the target is increased in a null or suitably sensitive genetic background. Such a target might be a membrane protein localized to the plasma membrane but it could include other membrane bound or soluble proteins localized to other organelles or sub-cellular compartments.

The system is primarily designed to provide stable, high level, functional expression of target membrane proteins. This is preferably achieved by engineering appropriate elements of the gene encoding the target membrane protein, together with a transcriptional terminator and a downstream selectable marker, into a chromosomal copy of a non-essential yeast gene which is also under the control of a transcriptional regulator. This type of construct, together with a control null mutant, provides a system in which potential and actual cell surface targets can be selectively and functionally overexpressed to facilitate the physiological and biochemical characterisation of such targets and their use for drug discovery purposes. The system also includes the possibility of functionally over-expressing membrane-bound or soluble proteins localized to other organelles or sub-cellular compartments The yeast *S. cerevisiae* is the preferred yeast host cell. *S. cerevisiae* provides a valuable system for drug discovery because its genome has been entirely sequenced and extensively annotated, its genetics are both well understood and tractable, while its ease of culture can allow cell-based assays compatible with the microtitre plate formats that are conventionally used for both manual and high throughput screening.

The present invention provides a system for over-expressing a heterologous membrane protein to a level so that said protein constitutes 10-20% of plasma membrane protein and is therefore sufficiently prominent to measure the effects of the test drugs. The successful high level (>10% of plasma membrane protein), heterologous expression of plasma membrane proteins in *S. cerevisiae* is accomplished for the first time. Previous attempts at heterologous expression of membrane proteins in various systems has not been successful (Mahanty et al 1994; Luo et al, 1999; Mao & Scarborough, 1997 and Huang et al 1996). One reason for this may be inappropriate intracellular trafficking that can be affected by growth medium and growth stage (de Kerchove d'Exaerde A, et al, 1995). Another reason may be incompatibility with endogenous systems responsible for the correct folding of newly synthesised protein products. In addition, these prior art used episomal vector based systems which require continuous selection and give variable results as individual organisms in a population can carry different loads of the vector. The incorporation of a single copy of the heterologous gene into the genome of the expressing organism as used in the present invention provides a defined and stable genetic load. Thus the present system which achieves a stable and high level functional expression of heterologous proteins in the plasma membrane without being compromised by mistrafficing and misfolding, therefore provides a considerable advantage over the prior art systems.

The present invention is thus directed to the use of *S. cerevisiae* and more particularly to mutant strains thereof which are genetically engineered to be deficient in selected membrane proteins, thereby providing a suitable null phenotype as a host cell in which to induce the overexpression of the target membrane protein. As an example, the strain AD1-8u⁻, which is deficient in 7 major ABC membrane transporters, has been identified and used as a suitable host cell in which to induce the over-expression of a heterologous target membrane protein. The AD1-8u⁻ strain is prepared in accordance with the teaching of Decottignes et al, 1998, in which this strain is referred to as AD12345678. In this host cell the phenotype provides susceptibility to the azole and triazole drugs plus a wide range of xenobiotics that use multidrug efflux pumps of the ABC transporter class. It is also envisaged that other drug susceptible or nutrient-requiring phenotypes may be created by the selective elimination of endogenous target transporters or enzymes in yeast or other cell types for use in the present invention as would be appreciated by a skilled worker.

The present invention also provides the genetic modification of the AD1-8u⁻ host strain to contain a sec6-4 mutation. Sec6-4 is a temperature sensitive mutation of *S. cerevisiae* which is permissive for the fusion of secretory vesicles with the plasma membrane at temperatures up to 30° C. At the non-permissive temperature of 37° C. the membrane fusion process is blocked and causes lethality after several hours. As expected, AD1-8u⁻ sec6-4 cells are fluconazole sensitive, grow normally at 30° C. but fail to grow at 37° C. Transformants of this host are therefore expected to overexpress genes encoding plasma membrane proteins inserted into the PDR5 locus at both 30° C. and 37° C. Thus a membrane protein destined for the plasma membrane, whose synthesis is induced by the interaction between the Pdr1-3p transcription factor and the PDR5 promoter, should be integrated normally into the plasma membrane at 30° C. but retained in secretory vesicles at 37° C. The resultant secretory vesicles are expected to be electrochemically active and their constituent integral membrane proteins oriented vectorially in the membrane. For example, elements of the cytoplasmic catalytic and nucleotide-binding domains of ABC-type multidrug efflux proteins should be exposed on the external face of the vesicles. Conversely, the extracellular elements of such plasma membrane proteins should project into the lumen of the secretory vesicle. These latter parts should only be accessible to membrane impermeant reagents if the lipid bilayer of the secretory vesicle is disrupted. This invention therefore includes the possibility of using whole cells, isolated plasma membranes and secretory vesicles to identify the molecular surface that binds membrane impermeant compounds and to assess the electrochemical properties of targeted membrane proteins. The functional hyper-expression of membrane proteins in secretory vesicles, particularly those proteins with transport and/or electrochemical function, provides a new tool to evaluate the properties of such molecules.

The plasmid vector used in the system of the present invention, was derived from the plasmid pSK-PDR5PPUS (FIG. 1) and includes the coding sequence of a target membrane protein whereby said sequence is under the control of a promoter and/or transcriptional regulator such that over-expression of the target protein is induced. The pdr1-3 mutation in the *S. cerevisiae* Pdr1p transcriptional regulator has been shown to hyper-induce the PDR5 gene promoter and cause high-level functional over-expression of the Pdr5p protein in yeast plasma membranes (Balzi E, et al, 1994; Carvajal E, et al, 1997; Decottignies A, et al, 1994). The system of the present invention effectively replaces the coding sequence of Pdr5p with the coding sequence of the target heterologous membrane protein plus a transcription terminator.

Figure 1A:
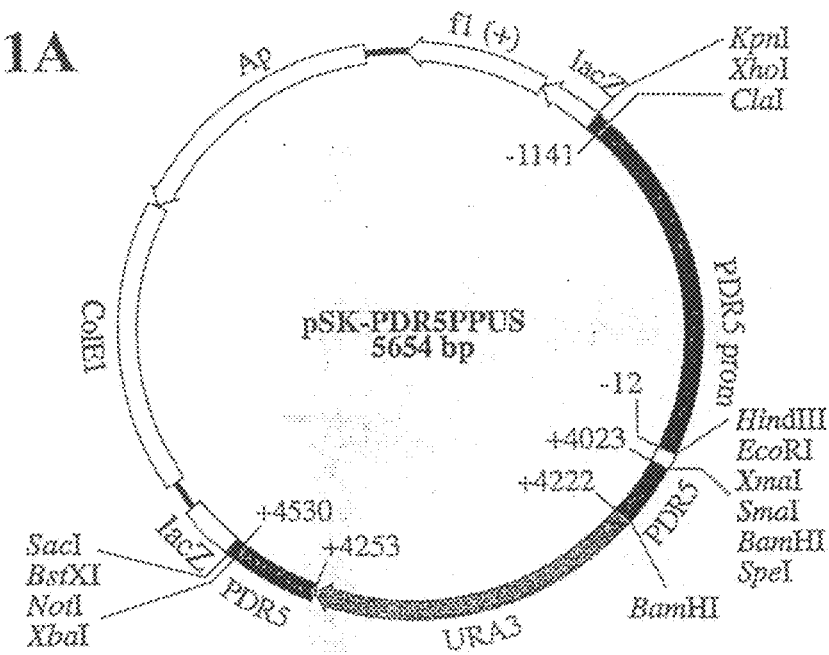
FIG. 1 (A) shows the structure of the pSK-PDR5PPUS plasmid and (B) shows the structure of the derivative plasmid pABC3.
Figure 1B:
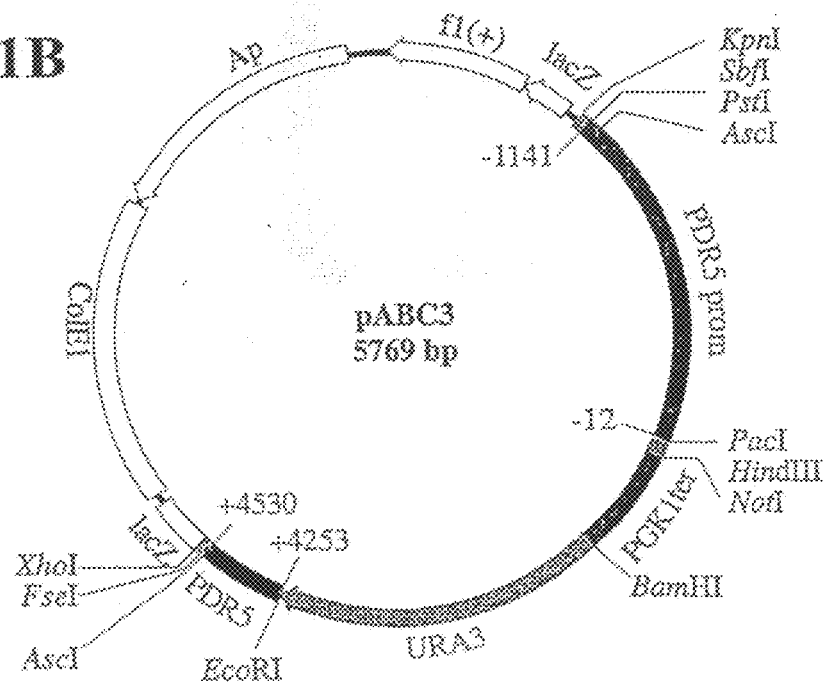

The pSK-PDR5PPUS plasmid was modified to improve its performance in the cloning of coding regions and in engineering yeast strains that hyper-express these constructs under the control of the Pdr1p transcription factor containing the pdr1-3 mutation (Pdr1-3p). FIG. 1B shows a new pABC3 vector based on the prototypic vector pSK-PDR5PPUS (FIG. 1A). Both vectors can replicate in *E. coli* but not in *S. cerevisiae*. In pABC3, pSK-PDR5PPUS has been modified to delete restriction sites between the HindIII and BamHI cutting sites in the original multicloning site and to insert the *S. cerevisiae* PGK1 transcriptional terminator. The pABC3 vector also includes several 8-base pair restriction enzyme recognition sites (SbfI and AscI immediately upstream of the PDR5 promoter, PacI and NotI near the junction between the PRD5 promoter and the PGK1 terminator and FseI downstream of the PDR5 ORF, and an EcoRI site downstream of the URA3 marker). These changes were incorporated to provide a universal yeast terminator, to aid in the production of vectors carrying alternative genetic markers, to assist the directional cloning of PCR products containing coding regions and to facilitate the excision from the vector of the PDR5-imbedded URA3-containing transformation cassette for the purpose of replacing the chromosomal PDR5 locus with the transformation cassette. It is also envisaged that the plasmid vector pSK-PDR5PPUS or it derivatives may be cloned into yeast centromeric or multicopy vectors, for example, to allow for high level inducible expression of membrane proteins in accordance with the present invention.

The pdr1-3 mutation was used in the system of the present invention to drive the stable over-expression of heterologous genes inserted into the *S. cerevisiae* genome at the PDR5 locus of genetically modified strains resulting in large amounts of the fully functional heterologous membrane protein being translated, transported to and incorporated into the plasma membrane of *S. cerevisiae*. However, a different transcription system regulator may be used to upregulate the expression of a target heterologous membrane protein as would be appreciated by a skilled worker. For example, the zinc cluster protein Rdr1p is a transcriptional repressor of the PDR5 gene and its deletion will therefore result in up-regulating at the PDR5 locus, while other mutations in the PDR1 gene are known to up-regulate expression at the PDR5 locus (Carvajal E, et al, 1997). In addition, alternative constitutive, inducible or controllable promoters might be used to control expression from the PDR5 locus in place of the PDR5 promoter. These include constitutive *S. cerevisiae* PDR5 and PAM1 promoters, copper controllable CTR3, glucose inducible ADH1 and PGK promoters, the galactose inducible GAL promoter, the doxycycline controllable bacterial tet0 promoter (Belli, G. et al, 1998) and the tet0::ScHOP1 controllable cassette (Nakayam H., et al, H. et al, 1998).

The mutated transcriptional regulator pdr1-3 is thought to affect expression of a number of genes that include the PDRE (pleiotropic drug responsive element) sequences and to also affect, either positively or negatively, the expression of some other yeast genes involved in intracellular trafficking of membrane proteins. PDR5 expression appears to be the most highly up-regulated among genes containing one or more upstream PDREs. However, it is considered that the coordinated expression of multiple genes affected by Pdr1-3p may be required for the functional expression of heterologous genes from the PDR5 locus.

The applicability of the present invention is illustrated in the examples below in which the pdr1-3 mutation is used to drive the stable high-level over-expression in *S. cerevisiae* of functional heterologous membrane proteins, namely Cdr1p, Cdr2p, Ben$^R$p and Erg11p from the pathogenic fungi *Candida albicans* and Cdr1p and Pdh1p from *Candida galbrata*. Cdr1p, Cdr2p and Pdh1p are membrane proteins of the ABC-transporter class related to the *S. cerevisiae* multidrug efflux pump Pdr5p (Prasad R, et al, 1995). Cdr1p is encoded by the gene most often associated with the fluconazole-resistance of *C. albicans* clinical isolates obtained from immunocompromised and debilitated patients (Sanglard D, et al 1995; Sang-lard D, et al 1997; White T C, 1997). Ben$^R$p (also referred to as Mdr1p) is a member of the Major Facilitator Superfamily of membrane transporters that use the electrochemical gradients of the plasma membrane to transport xenobiotics such as fluconazole (Fling M E, et al, 1991). Although conferring drug resistance by transporting fluconazole out of fungal cells, it has a narrower substrate specificity for azole drugs than Cdr1p (Sanglard D, et al, 1995, Sanglard D, et al, 1996). Erg11p is the lanosterol α-14 demethylase of ergosterol metabolism in fungi and is the target of fluconazole action (for review see White T C, et al, 1998). Over-expression sufficient to demonstrate drug resistant phenotypes of considerable practical value was achieved by replacing the chromosomal copy of the PDR5 ORF (open reading frame) with the ORF of *C. albicans* CDR1 or BEN$^R$ or ERG11 in a pdr1-3 mutant depleted in endogenous membrane transporters. The invention is also illustrated by the properties of the mutant *S. cerevisiae* strain which additionally contains the sec6-4 mutation. The value of such heterologous expression systems in studies to determine pump specificity and to screen for pump antagonists is illustrated. However, other applications of this and derivative systems may be carried out as would be appreciated by a person skilled in the art. Such potential applications include uses related to the heterologous over-expression of P-glycoprotein, the cystic fibrosis transmembrane conductance regulator, and other human, animal, microbial, plant and fungal plasma membrane proteins that can be used in the treatment of disease, and the modulation of physiology, growth or development. The invention may also find application in the over-expression of heterologous membrane proteins for the purposes of biochemical or structural analysis of the expressed membrane proteins, enzyme purification and pharmacogenomic applications. A further application of the system which is contemplated is the use of panels of isogenic yeast comprising a susceptible control strain plus a set of constructs that individually functionally hyper-express molecules that provide separate resistant determinants. For example a panel of mutants comprising the AD1-8u$^-$ mutant and derivative strains individually hyper-expressing Cdr1p or other ABC-pumps, Ben$^R$p or other MFS pumps, and Erg11p could be used to select for antifungal agents that would not be susceptible to mechanisms of resistance mediated by these molecules. The panel of strains could be used to select drugs whose intracellular targets either involved, or did not involve Erg11p, and to identify compounds whose potency is not compromised by the expression of multidrug efflux pumps. This could be applied to either the identification of new classes of drugs or the refinement of existing classes of drugs.

In a further embodiment the present invention provides a kit for screening for drugs useful as a pharmaceutical or agrochemical comprising:
(i) a host cell comprising a mutant strain deficient in one or more naturally occurring drug efflux pump proteins;
(ii) a vector containing the coding sequence of a target heterologous membrane protein, said sequence being under the control of a promoter which, upon transformation of said host cell and chromosomal integration, causes over-expression of the functional target protein in the membrane of the host cell, wherein said functional target protein is expressed prominently in the membrane of the host cell and is accessible for drug screening applications; and
(iii) instructions to carry out said transformation and drug screening procedures.

The host cell is of the genus *Saccharomyces*, and most preferably the host cell is a *Saccharomyces* cell which has been genetically altered to be depleted in one or more natural membrane proteins. A suitable host cell is the *Saccharomyces*

*cerevisiae* AD1-8u⁻ strain. In another embodiment a suitable host cell may be a sec6-4 mutant of the AD1-8u⁻ strain. In a further embodiment the host strain may be a derivative of the AD1-8u⁻ strain modified to select for a novel phenotype, such as prototrophy, an auxotrophic requirement of drug sensitivity.

The vector may contain elements which allow replication in *Escherichia coli*, plus a promoter such as a *Saccharomyces cerevisiae* promoter and more preferably the PDR5 promoter. Activity of the *Saccharomyces* promoter is preferably under the additional control of a mutated transcriptional regulator causing over-expression of the target coding sequence, leading to abnormal expression of the target protein in the membrane of the host cell. The mutated transcriptional regulator Pdr1-3p is preferred and is located in the genome of the host cell. In some applications, a transcriptional terminator that is functional in yeast may be included in the vector. Either the natural terminator of the gene encoding the membrane protein or the yeast PGK1 terminator is preferred. In other applications immunological, affinity or fluorescent tags may be included in the vector. In some further applications, a selectable marker may also be included in the vector such as *S. cerevisiae* URA3 marker. In other applications a *S. cerevisiae* centromere or autonomously replicating sequence might be included in the vector. The vector is preferably pABC3.

Non-limiting examples of the application of this technology, most particularly to the understanding of multidrug efflux at the cellular and biochemical level, together with the characterisation of inhibitors that are active against prominent fungal pathogens, are set out below.

EXAMPLES

Example 1

Production of Plasma Membrane Protein Expression System Validated by *C. albicans* Cdr1p Expression in *S. cerevisiae*

Materials and Methods
Bacterial and Yeast Strains, and Growth Media.
Plasmids were maintained in *Escherichia coli* DH5a. The CDR1 gene was obtained from *C. albicans* ATCC 10261. *S. cerevisiae* strains used were: AD1-8u⁻ (MTα, pdr1-3, his1, ura3, Δyor1::hisG, Δsnq2::hisG, Δpdr5::hisG, Δpdr10::hisG, Δpdr11::hisG, Δycf1::hisG, Δpdr3::hisG, Δpdr15::hisG, based on AD12345678 [Decottignies, A. et al, 1998]) and AD124567 (MATα, pdr1-3, his1, Δyor1::hisG, Δsnq2::hisG, Δpdr10::hisG, Δpdr11::hisG, Δycf1::hisG, Δpdr3::hisG [Decottignies A, et al, 1998]). *E. coli* was cultured in LB medium (Sambrook J, et al, 1996). *C. albicans* was maintained on YEPD (g/l: yeast extract 10, bacto peptone 20, glucose 20), and *S. cerevisiae* was maintained on YEPD, complete synthetic medium (CSM, Bio 101, Vista, Ca.) or CSM without uracil (CSM-URA, Bio 101) as required.

Figure 2:
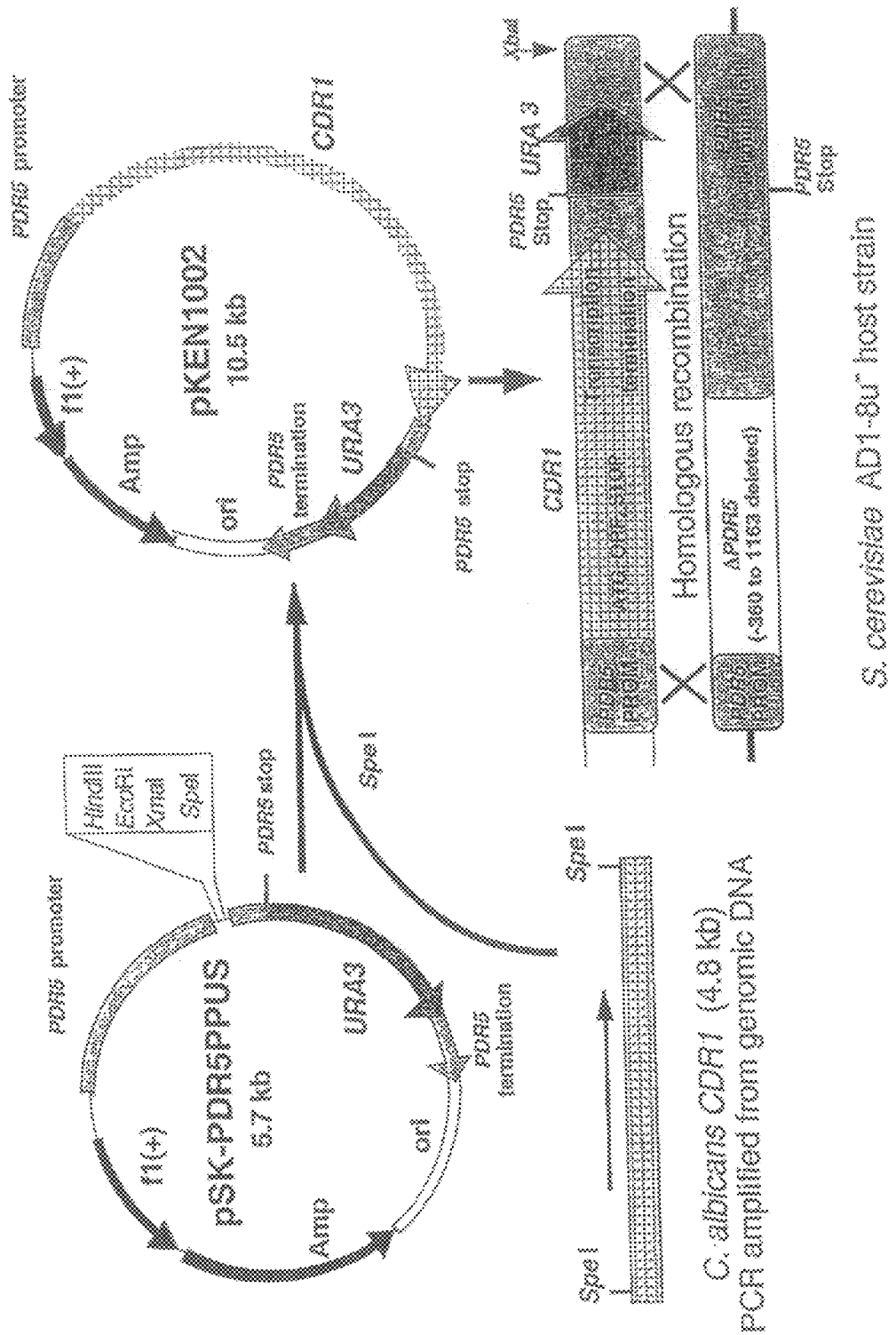
FIG. 2. (A) shows the construction of plasmid pKEN1002 and the integration of the *C. albicans* CDR1 gene at the chromosomal PDR5 locus of *S. cerevisiae* AD1-8u⁻

Plasmid Construction and Yeast Transformation.
Expand DNA polymerase (oche Diagnostics N.Z. Ltd, Auckland, N.Z.) was used to PCR amplify the CDR1 ORF and transcriptional termination region (4.8 kb) from *C. albicans* ATCC 10261 genomic DNA using primers containing SpeI restriction sites: 5'-CTTTAAAAGGTCAACTAG-TAAAAAATTATG-3' (SEQ ID NO: 1) and 5'-CAATAATA-CACTAGTTTGCAACGGAAG-3' (SEQ ID NO: 2). The PCR product was digested with SpeI and cloned into plasmid pSK-PDR5PPUS (FIG. 1A) that had been previously cut with SpeI and dephosphorylated with alkaline phosphatase (New England Biolabs, Beverly, Mass.). The orientation of the CDR1 open reading frame (ORF) was confirmed by sequencing to be the same as PDR5 and the plasmid was designated pKEN1002. Plasmid pKEN1002 (FIG. 2A) was linearized with XbaI and used to transform *S. cerevisiae* AD1-8u⁻ to Ura⁺ by the lithium acetate transformation protocol (Alkali-Cation Yeast kit, Bio-101). The entire CDR1ORF DNA in pKEN1002 was sequenced, and the CDR1 ORFs from *C. albicans* ATCC 10261 and *S. cerevisiae* AD1-8u⁻/pKEN1002 transformant AD1002 were PCR amplified from genomic DNA with Pfx.DNA polymerase (Gibco BRL, Life Technologies, Rockville, Md.) and sequenced.

Northern Analysis of RNA Extracted from *S. cerevisiae*.
Total RNA was extracted from *S. cerevisiae* as described previously (Albertson G D, et al, 1996). RNA (20 µg) was electrophoresed in agarose gels, vacuum blotted onto Hybond⁺ nylon membrane (Amersham Pharmacia Biotech New Zealand, Auckland, N.Z.) and fixed by UV irradiation. Membranes were hybridized with [α-$^{32}$P]dCTP-labeled probes under high stringency conditions as previously described (Cannon R D, et al., 1994). A *C. albicans* CDR1 probe (ORF nt 1-497) was generated by PCR amplification and the *S. cerevisiae* PMA1 probe (ORF nt-835-1598) was obtained as a 2.4 kb BamHI fragment from plasmid pDP100 (Seto-Young, D. et al, 1994).

Immunodetection of *C. albicans* Cdr1p.
Crude protein extracts were prepared from *S. cerevisiae* cells grown in YEPD broth to mid-exponential phase. Plasma membrane fractions of these cells were obtained by sucrose gradient centrifugation as previously described (Monk, B C. et al., 1991). Protein samples (40 µg) were separated by electrophoresis in 8% SDS polyacrylamide gels and either stained with Coomassie blue or electroblotted (100 V, 1 hour, 4° C.) onto nitrocellulose membranes (Highbond-C, Amersham). Western blots were incubated with a 1:200 dilution of anti-Cdr1p antibodies (provided by Dr D. Sanglard, University Hospital Lausanne, Switzerland). Immunoreactivity was detected using horseradish peroxidase-labeled swine anti-rabbit IgG antibodies at a 1:500 dilution.

Genomic DNA Extraction and Southern Analysis of the *C. albicans* CDR1 Gene Integrated into the *S. cerevisiae* Genome.

Genomic DNA was prepared from *S. cerevisiae* cells as described previously (Scherer, S, and Stevens, D A. 1987). Genomic DNA (5 µg) was digested with the restriction endonucleases EcoRV, SpeI, BamHI, PstI or EcoRI (NEB), separated in a 0.75% agarose gel, and transferred to Hybond⁺ nylon membrane (Amersham). Membranes were hybridized with [α-$^{32}$P]dCTP-labeled *C. albicans* CDR1 probe under high stringency conditions (Cannon, R D. et al, 1994).

Results
Integration of the *C. albicans* CDR1 gene at the PDR5 locus in *S. cerevisiae* AD1-8u⁻. The function of *C. albicans* Cdr1p was studied with a diminished background of endogenous ABC transporter interference by expressing CDR1 in the *S. cerevisiae* pdr1-3 mutant AD1-8u⁻ that is deleted in 7 major ABC transporters. This was achieved by adapting the pleiotropic drug resistance (PDR) pathway-based membrane protein over-expression system (Decottignies A, et al, 1998) that utilizes the multidrug resistance regulatory mutation pdr1-3 to up-regulate the PDR5 promoter and results in over-expression of the Pdr5p protein in plasma membranes (Balzi E, et al, 1994; Decottignies A, et al, 1994). Hyper-induction of Cdr1p was achieved by integrating the CDR1 ORF at the *S. cerevisiae* AD1-8u⁻ PDR5 locus downstream from the PDR5 promoter. First, the CDR1 ORF and its transcription terminator region was PCR amplified from *C. albicans* ATCC 10261 genomic DNA with a high fidelity polymerase and cloned into the SpeI site in plasmid pSK-PDR5PPUS, which is located between the PDR5 promoter and PDR5 stop codon (FIG. 1). The resulting plasmid, pKEN1002 (FIG. 2) was linearized with XbaI and transformed into *S. cerevisiae* AD1-8u⁻ (ΔPDR5: nt 360-1163 deleted) with selection for Ura⁺ transformants. This selection protocol was made possible by the presence of the *S. cerevisiae* URA3 gene in the PDR5 terminator region of pKEN1002.

Figure 3:
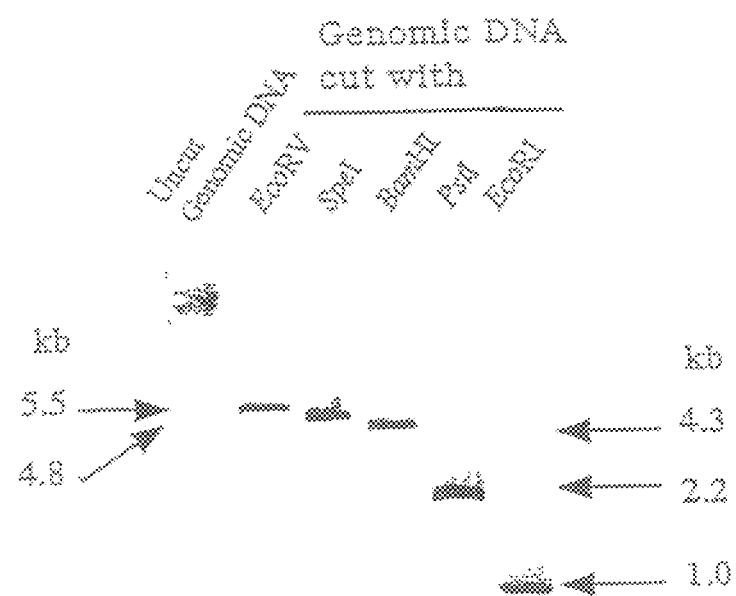
FIG. 3. shows confirmation of the integration of a single copy of *C. albicans* CDR1 at the PDR5 locus in *S. cerevisiae* AD1002. Intact or endonuclease-restricted AD1002 genomic DNA was electrophoresed in an agarose gel, vacuum blotted onto nylon membrane and hybridised with $[\alpha$-$^{32}$P]dCTP-labeled *C. albicans* CDR1 probe under high stringency conditions.

The Ura⁺ *S. cerevisiae* transformants demonstrated lower sensitivities to azoles than the parental strain, and one (AD1002) was selected for further analysis. The doubling time of AD1002 in YEPD and CSM-based media was the same as for the parental strain. To confirm integration of CDR1 at the PDR5 locus in AD1002, uncut total DNA and restricted genomic DNAs were hybridized with a *C. albicans* CDR1 probe (FIG. 3). The probe hybridized with uncut genomic DNA and there was no evidence of an episomal plasmid. Hybridization of the probe with single bands of genomic DNA of expected size after digestion with five separate restriction endonucleases (EcoRV, 5467 bp; SpeI, 4776 bp; BamHI, 4272 bp; PstI, 2236 bp; EcoRI, 1042 bp) indicated that a single integration event had occurred at the PDR5 locus. The CDR1 gene from the donor strain *C. albicans ATCC* 10261 was sequenced and compared with the sequence from *C. albicans* strain 1001 (Prasad R, et al, 1995, Genbank accession number X77589). There were 45 nucleotide differences (over the 4503 nt ORF) between the two DNA sequences, but only two amino acid changes: F427Y and V916I substitutions in ATCC 10261 (see Table 1 below). The paucity, and conservative nature, of the amino acid substitutions indicates that the CDR1 gene is functionally highly conserved between strains. The CDR1 gene from plasmid pKEN1002, which had been passaged through *E. coli*, had 21 nucleotide differences from the template ATCC 10261 sequence but only 5 amino acid differences: E214Q, S842T, S1021L, E1177K, and A1416E substitutions in pKEN1002. By contrast, there were no nucleotide differences between CDR1 amplified from the *S. cerevisiae* AD1002 transformant and the CDR1 sequence in plasmid pKEN1002 used in the transformation. This is consistent with the fidelity of the DNA polymerase used to amplify the gene from genomic DNA, and suggests that the differences between the pKEN1002 and *C. albicans* ATCC 10261 CDR1 sequences comprise allelic differences (see Example 3), a low frequency of changes caused by PCR and mutations that were selected in *E. coli*. None of the CDR1 sequences (*C. albicans* 1002, *C. albicans* ATCC 10261, pKEN1002 or *S. cerevisiae* AD1002) contained the CTG codon which is decoded by *S. cerevisiae* as leucine, but by *C. albicans* as serine. Substitution of leucine for serine in Cdr1p heterologously expressed in *S. cerevisiae* AD1002, with consequential effects on protein function, is not therefore a problem.

Expression of *C. albicans* CDR1 in *S. cerevisiae* AD1002.

The expression of *C. albicans* CDR1 in AD1002 was investigated by a Northern analysis and by immunodetection of plasma membrane proteins. The expression of PMA1 and CDR1 mRNAs by *S. cerevisiae* AD1-8u⁻, and by this strain transformed with pSK-PDR5PPUS or pKEN1002 (AD1002) was measured. PMA1 mRNA, encoding the constitutively expressed plasma membrane H⁺-ATPase, was expressed in all strains (FIG. 4A). CDR1 mRNA was expressed only in cells transformed with pKEN1002. Expression of Cdr1p (FIG. 4B) was examined by SDS-PAGE analysis of plasma membrane proteins from these strains and *S. cerevisiae* AD124567 which over-expresses Pdr5p (Decottignies A, et al, 1994). No major plasma membrane protein bands of the size expected for ABC transporters (170 kDa [Decottignies A, and A. Goffeau, 1997; Krishnamurthy, et al, 1998; Prasad R, et al, 1995]) were detected by coomassie blue staining of samples from the parental strain AD1-8u⁻. This confirmed the depletion of endogenous pumps in this multiply-deleted strain. In contrast, samples from both AD1002 and AD124567 contained a major protein band at 170 kDa which accounted for 10-20% of Coomassie-stained plasma membrane protein. Only the 170 kDa protein from AD1002 reacted with anti-Cdr1p antibodies (FIG. 4C).

Example 2

Characterisation of a Protein Over-Expressed Using the System Described in Example 1

Materials and Methods
Construction of the AD1-8u⁻ sec6-4 Mutant Strain

Construction of this strain involved the transformation of the AD1-8u⁻ strain (containing the wild type SEC6 gene) with a URA3 marked version of the sec6-4 mutant gene, followed by the selective removal of the URA3 marker. In the first step of the procedure the URA3-dp1200 cassette of plasmid pDDB57 (Wilson et al., Yeast 16:65-70, 2000) was used to temporarily mark the SEC6-4 mutant gene in *S. cerevisiae* strain SY1 (Potenza et al., Yeast 8:549-548, 1992). The URA3-dp1200 cassette contains *C. albicans* URA3 and direct repeat sequences of 201 bp flanking the URA3 marker. This feature allows looping out of the chromosomally integrated URA3 gene by homologous recombination. The cassette also includes 77 bp upstream and 144 bp downstream of the two repeat sequences, respectively. The URA3-dp1200 cassette was amplified by PCR as a 1296 bp fragment using the following DNA oligonucleotide primers: +ve strand primer: 5'-TCCCGTCTAGTTAATCACTCGGAAG-GAAACAACGAGTGAGGTTT CGTGTCATTCTCTA-GATTTTCCCAG-TCACGACGTT-3' (SEQ ID NO: 3) and negative strand primer 5'TGCTACCAAGCTAACAAAAG-

TABLE 1

Nucleotide and amino acid similarities between CDR1 sequences from
*C. albicans* 1001, *C. albicans* ATCC 10261, plasmid pKEN1002 and *S. cerevisiae* AD1002

| | | % CDR1 DNA similarity (N° nucleotide substitutions) | | | |
|---|---|---|---|---|---|
| | | *C. albicans* 1001 | *C. albicans* 10261 | pKEN1002 | *S. cerevisiae* AD1002 |
| % Cdr1p amino acid similarity (N° amino acid substitutions) | *C. albicans* 1001 | | 99.00 (45) | 98.62 (62) | 98.62 (62) |
| | *C. albicans* 10261 | 99.87 (2) | | 99.53 (21) | 99.53 (21) |
| | pKEN1002 | 99.53 (7) | 99.67 (5) | | 100 (0) |
| | *S. cerevisiae* AD1002 | 99.53 (7) | 99.67 (5) | 100 (0) | |

GATCAGGCTGC-CCAAACGGACGTAGACTCAC TGGGCTCCG TGTGGAATTGTGAGCGGATA-3' (SEQ ID NO: 4). The oligonucleotide sequences homologous to the pDDB57 cassette are underlined. The remaining 60 nucleotides each of primer direct the URA3-dp1200 cassette to integrate, at 293 bp to 352 bp for the +ve strand primer and at 412 bp to 353 bp for the 3'–ve strand primer, downstream of the TAA stop codon of the SEC6 or SEC6-4 mutant gene in S. cerevisiae. Uracil prototrophs of strain SY1 were selected after directed integration of the URA3-dp1200 PCR fragment, via homologous cross-over, downstream of SY1 sec6-4. The strain designated SY1::URA3 was verified using PCR using primers flanking the expected integration site (+ve strand primer fpS: TCCAGAGAGTATAACTCCTG (SEQ ID NO: 5) and –ve strand primer SUB2: TGTTG-GAAATTTCTCCCGTG) (SEQ ID NO: 6). The SEC6-4-URA3 construct in strain SY1::URA3 was PCR amplified from genomic DNA (+ve strand primer SUB1 AATGCAG-GAGTTTTACAGTGGC (SEQ ID NO: 7) and –ve strand primer SUB2 as above). The SUB1 sequence is located immediately 3' to the upstream ORF and SUB2 immediately 5' to the downstream ORF adjacent to the SEC6 gene, respectively. The resultant 5317 bp PCR fragment, containing the whole SEC6-4 gene plus the URA3-dp1200 cassette, was purified and used to transform strain AD1-8u⁻ to uracil prototrophy, by replacement of its chromosomal copy of SEC6. The correct directional integration of the PCR fragment, via homologous double cross-over at the SEC6 locus, was confirmed by PCR for all uracil prototrophic transformants (using the primers that verified the construct in strain SY1::URA3). These ura+ transformants were then tested for the expected temperature sensitive growth phenotype, to verify replacement of SEC6 in AD1-8u⁻ with the SECc6-4 allele of strain SY1. A representative transformant, designated AD1-8u⁻ sec6-4::URA3, was plated onto CSM agar containing 5'-fluoro-orotic acid (5'-FOA) for selective loss of the URA3 marker (Boeke et al., Mol Gen Genet 197:345-346, 1984). Strains that looped out the URA3 cassette, via a single homologous cross-over between the 201 bp direct repeat regions, were recovered from these plates. Ura⁻ colonies were verified using the PCR primer pair fp5/SUB2, in comparison with strains SY1::URA3, AD1-8u⁻ SEC6::URA3 and AD1-8u⁻-sec6-4::URA3. All the ura colonies gave the expected 422 bp PCR fragment which comprises one copy of the 201 bp direct repeat sequence of the URA3-dp1200 cassette, the 77 bp upstream of the 5' direct repeat and the 144 bp downstream of the 3' direct repeat. A representative strain was designated AD1-8u⁻-sec6-4::200.

Minimum Growth Inhibitory Concentration (MIC) Determination.

The MICs of antifungal agents for S. cerevisiae cells were determined by a microdilution test based on the macrodilution reference method of the National Committee for Clinical Laboratory Standards. Cells (10 µl cell suspension, 2×10⁵ cells/ml) were inoculated into 90 µl CSM-URA, buffered with 10 mM 2-(N-morpholino)ethanesulfonic acid (MES) and 18 mM N-2-hydroxyethylpiperazine-N'-2-ethanesulfonic acid (HEPES), pH 7.0 and containing 0.67% (w/v) yeast nitrogen base (YNB) in microtitre plate wells. For the uracil-requiring strain AD1-8u⁻ the medium was supplemented with 0.02% (w/v) uridine. The wells contained, in 200 µl, doubling dilutions of antifungal agents (final concentrations: fluconazole, 40-0.078 µg/ml; itraconazole and ketoconazole, 8-0.016 µg/ml). The microtitre plates were incubated at 30° C. for 48 h with shaking and then the growth of cells in individual wells (OD₅₉₀) was measured with a microplate reader (EL 340, Bio-Tek, Winooski, Vt.). The MIC₈₀ was the lowest concentration of drug that inhibited growth yield by at least 80% compared to a no-drug control.

Nucleotide Triphosphatase Assays.

Yeast were grown in YEPD, pH 5.5 at 30° C. until they reached late-exponential phase of growth (OD₆₀₀ nm=7), washed twice in ice-cold distilled water, and incubated on ice for 30 min to minimize glucose-stimulated Pma1p activity. Cells were resuspended in homogenising medium (50 mM Tris pH 7.5, 2 mM EDTA and 1 mM phenylmethylsulfonyl fluoride) and disrupted using a Braun Homogeniser. Cell debris and unbroken cells were removed by centrifuging at 2,000×g at 4° C. for 10 min. A crude membrane fraction was isolated from the cell-free supernatant by centrifuging at 30,000×g at 4° C. for 45 min. Plasma membranes were prepared by centrifugation of the supernatant obtained after selective precipitation of mitochondria at pH 5.2 as described previously (Goffeau, A. and Dufour, J. P., 1988). The plasma membranes were resuspended in 10 mM Tris pH 7.0, 0.5 mM EDTA and 20% [v/v] glycerol and stored at –80° C. Protein was determined using a micro-Bradford (Bio-Rad Laboratories, Hercules, Calif. [Bradford, M. M., 1976]) assay with gamma-globulin as standard. Nucleotide triphosphatase activity was measured by incubating the plasma membrane fractions (10 µg) at 30° C. in a final volume of 120 µl containing 6 mM NTP, 7 mM MgSO₄ in 59 mM MES-Tris buffer pH 6.0-8.0. To eliminate possible contributions from nonspecific phosphatases, vacuolar, or mitochondrial ATPases, 0.2 mM ammonium molybdate, 50 mM KNO₃ and 10 mM NaN₃, respectively, were included in assays (Monk B C, et al, 1991). Other ATPase inhibitors (20 µM oligomycin, 20 µM aurovertin B or 100 µM vanadate were added to the reaction where indicated. After 30 min the reaction was stopped by adding 130 µl of a solution containing 1% (w/v) SDS, 0.6 M H₂SO₄, 1.2% (w/v) ammonium molybdate and 1.6% (w/v) ascorbic acid. Inorganic phosphate released from NTPs was measured at 750 nm after 10 min incubation at room temperature.

Disk Drug Susceptibility Assays.

Drug susceptibility was measured using disk assays on CSM-URA plates (containing 1.5% w/v agar). Plates were seeded with yeast cells suspended in top agar (5 ml, 10⁵ cells/ml). For the uracil-dependent parental strain, agar was supplemented with 0.02% uridine. Five microliters of drug solution or solvent control were spotted onto sterile Whatman paper disks on the top agar. The following amounts (nmoles) of drugs were applied to individual disks: fluconazole, 6.5 (Pfizer Ltd., Sandwich, Kent, United Kingdom); ketoconazole, 0.094 (Janssen Research Foundation, Beerse, Belgium); itraconazole, 0.35 (Janssen); miconazole, 0.084 (Janssen); amphotericin B, 54 (E. R. Squibb & Sons, Princeton, N.J.); rhodamine 6G, 10 (Sigma, Penrose, Auckland, N. Z.); rhodamine 123, 50 (Sigma); trifluoperazine 100 (Sigma); benomyl, 10 (Nippon Roche); cycloheximide, 5 (Sigma); carbonyl cyanide p-chlorophenylhydrazone, 490 (CCCP, Sigma); oligomycin, 10 (Sigma); nigericin, 100 (Sigma); tamoxifen, 25 (Sigma); naftifine, 50 (Novartis); quinidine, 500 (Sigma); valinomycin, 20 (Sigma); verapamil, 1000 (Sigma). Agar plates were incubated at 30° C. for 48 h or until clear growth inhibition zones were visible.

Results

Antifungal Sensitivities of S. cerevisiae Cells Expressing C. albicans Cdr1p.

The phenotypic effects on antifungal sensitivity of Cdr1p expression in S. cerevisiae strains with a depleted ABC-transporter background was measured. The parental strain AD1-8u⁻ was exquisitely sensitive to fluconazole, ketoconazole and itraconazole (see Table 2 below). Transformant AD1002 was significantly less sensitive to fluconazole, ketoconazole and itraconazole, with >45-, >31- and >250-fold increases in MICs, respectively (Table 2). Thus, expression of Cdr1p in this transformant conferred cross-resistance to different azole antifungal drugs, as has been shown in other *S. cerevisiae* strains and in *C. albicans* (Albertson G D, et al, 1996; Prasad R, et al, 1995). These results together with the SDS-PAGE, Western and Northern analysis indicated that the *C. albicans* drug resistance gene CDR1 is functionally over-expressed in *S. cerevisiae* AD1002.

TABLE 2

Antifungal sensitivities of *S. cerevisiae* cells expressing Cdr1p or Cdr2p

| S. cerevisiae strain | MIC$_{80}$ (µg/ml) | | |
|---|---|---|---|
| | Fluconazole | Ketoconazole | Itraconazole |
| AD1-8u$^{-a}$ | 0.625 | <0.016 | <0.016 |
| AD1002$^b$ | 30 | 0.5 | 4 |
| AD1-8/CDR2 | 64 | 2 | 1 |
| AD1-8 sec6-4 | 0.5 | ND | ND |
| AD1-8 sec6-4/CDR1 | 80 | ND | ND |

$^a$Parental strain.
$^b$Strain expressing Cdr1p (the MIC values were unaffected by supplementing the medium with uridine [0.02% w/v]).
ND, not determined. These experiments were conducted at 30° C.

In a further set of experiments *C. albicans* CDR1 was hyper-expressed in AD1-8 sec6-4 and *C. albicans* CDR2 was hyper-expressed in AD1-8u$^-$ (see below). Comparison of the isogenic null and hyper-expressing strains showed increased resistance to azole drugs due to the high level expression of *C. albicans* CDR2 in the AD1-8 background or CDR1 in the AD1-8u$^-$ sec6-4 background (Table 2). These results demonstrate the functional expression of Cdr2p in the AD1-8 background and that Cdr1p is functional in the sec6-4 derivative of the AD1-8 strain when expressed under permissive conditions (30° C.). This sec6-4 mutant did not grow at 37° C., an ultimately lethal condition that leads to the accumulation of secretory vesicles that are unable to fuse with the plasma membrane.

*C. albicans* Cdr1p-Mediated Resistance to a Variety of Drugs.

Figure 5:
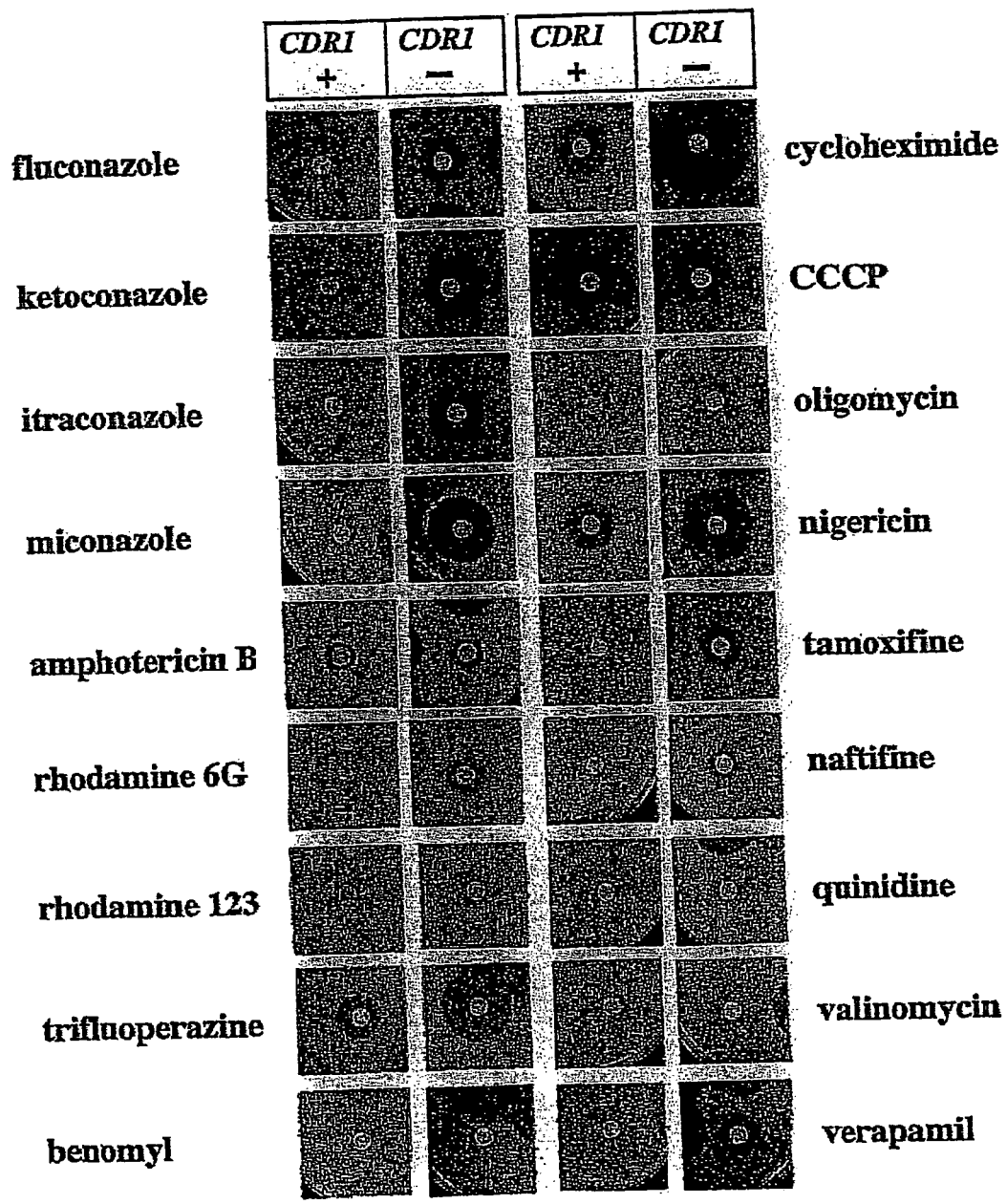
FIG. 5. shows the sensitivity of *S. cerevisiae* AD1002, expressing Cdr1p, to various drugs and chemicals. *S. cerevi-* siae AD1-8u⁻ (CDR1-) or AD1002 (CDR1+) cells (5×10⁵) seeded in top agar on CSM agar plates (containing uracil for AD1-8u⁻) were exposed to drugs or chemicals applied to filter disks and incubated at 30° C. for 48 h. The sensitivity of AD1002 to drugs or chemicals was unaffected by supplementing the medium with uridine (0.02% w/v). Amounts of individual drugs applied to disks are given in the Materials and methods section of Example 2, below.

The sensitivities of the parental *S. cerevisiae* AD1-8u$^-$ strain to a variety of drugs was compared with those of its transformed derivative AD1002 in order to assess the function of Cdr1p (FIG. 5). The differential sensitivities of these two strains is likely to be due to the drug efflux driven by Cdr1p. AD1002 showed cross-resistance to all azoles tested, and to the sterol biosynthesis inhibitor naftifine, but not to the antifungal amphotericin B.

Amphotericin B directly permeabilises the plasma membrane of yeast via an interaction with ergosterol. As expected, its toxicity in yeast was not modified by the over-expression of a multidrug efflux pump.

Transformant AD1002 showed clear resistance to the fluorescent dyes rhodamine 6G and rhodamine 123, with rhodamine 6G showing greater cytotoxicity for the parental *S. cerevisiae* strain. These dyes have been reported to be transported by mammalian P-glycoprotein and *S. cerevisiae* Pdr5p and Yor1p (Kolaczkowski M, et al, 1996, Decottingnies A, et al, 1998) but PDR5 and YOR1 are deleted in both AD1-8u$^-$ and AD1002. Rhodamine 6G and rhodamine 123 are therefore likely to be substrates for Cdr1p (Clark F S, et al, 1996; Maesaki S, et al, 1999).

It was further discovered that Cdr1p confers resistance to growth inhibition by the following drugs: the MDR modifier trifluoperazine; protein synthesis inhibitor cycloheximide; ionophoric peptide nigericin; anticancer drug tamoxifen; and calcium channel blocker verapamil. The structures and targets of these drugs are diverse and our results indicate that Cdr1p has a wide pumping specificity. The drug resistance phenotypes conferred by Cdr1p were similar to those observed in the over-expression of Pdr5p (Kolaczkowski M, et al, 1996). The parental strain AD1-8u$^-$ was resistant to the remaining drugs: tubulin synthesis inhibitor benomyl; mitochondrial ATPase and Pdr5p inhibitor oligomycin; potassium channel blocker quinidine; and K$^+$-selective ionophoric cyclodepsipeptide valinomycin at the concentrations used in this study which suggests that these drugs are not substrates of Cdr1p.

Nucleotide Triphosphatase Activity of AD1002.

Plasma membrane fractions from *S. cerevisiae* AD1002 possessed at least an order of magnitude higher oligomycin-sensitive ATPase activity than the parental strain AD1-8u$^-$ over the pH range 6.0-8.0 (FIG. 6). This activity had a pH optimum of around 7.5 and thus was readily distinguished from the Pma1p ATPase of *S. cerevisiae* which has a pH optimum of about 6.0 (Decottignies A, et al, 1994). Furthermore, the activity of Pma1p is insensitive to oligomycin (Monk B C, et al, 1991) and is specific for ATP (Decottignies A, et al, 1994). *C. albicans* Cdr1p expressed in *S. cerevisiae* AD1002 also showed oligomycin-sensitive UTPase, CTPase and GTPase activities similar to the ATPase activity, and all these NTPase activities had a slightly alkaline pH optima (see Table 3 below). Each NTPase activity of AD1002 was sensitive to 100 µM vanadate, but insensitive to 20 µM aurovertin B. Mitochondrial ATPase activity therefore made a negligible contribution to the ATPase activity of these membrane preparations.

TABLE 3

Oligomycin-sensitive NTPase activities in plasma membrane fractions of parental strain *S. cerevisiae* AD1-8u$^-$ and *S. cerevisiae* AD1002, expressing Cdr1p

| | Oligomycin-sensitive NTPase activity (nmole Pi min$^{-1}$ mg protein$^{-1}$)$^a$ | | | | | |
|---|---|---|---|---|---|---|
| | UTPase | | CTPase | | GTPase | |
| S. cerevisiae strain | pH 6.5 | pH 7.5 | pH 6.5 | pH 7.5 | pH 6.5 | pH 7.5 |
| AD1-8u$^-$ | 1 | 0 | 1 | 0 | 0 | 0 |
| AD1002 | 16 | 30 | 24 | 40 | 27 | 46 |

Figure 4:
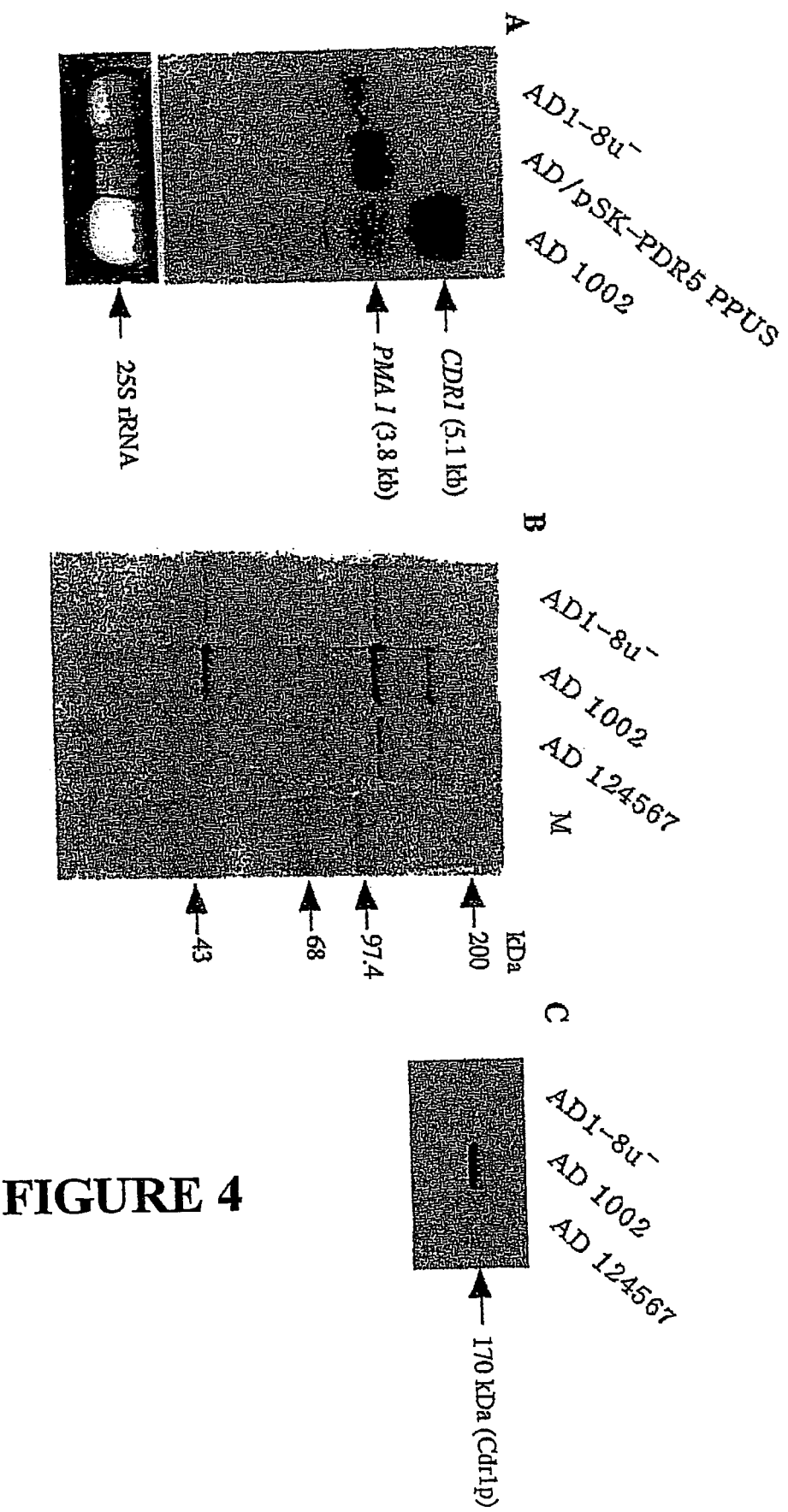
FIG. 4. shows expression of *C. albicans* CDR1 mRNA and Cdr1p in *S. cerevisiae* AD1002. (A) RNA obtained from the parental strain AD1-8u⁻, AD1-8u⁻ transformed with linearised plasmid pSK-PDR5PPUS, or AD1002 was hybridized with a mixture of $[\alpha$-$^{32}$P]dCTP-labeled *C. albicans* CDR1 and *S. cerevisiae* PMA1 (control) probes. The lower panel shows a portion of the ethidium bromide stained agarose gel before vacuum blotting. (B) Plasma membrane proteins separated through 8% polyacrylamide gel and stained with Coomassie blue. (C) Plasma membrane proteins separated through 8% polyacrylamide gel were electroblotted onto nitrocellulose and incubated with anti-*C. albicans* Cdr1p antibodies. Antibodies were detected using a horseradish peroxidase-IgG complex.

$^a$NTPase activities were determined in assays similar to those providing the data presented in FIG. 4. Values represent the differences in ATPase activities measured in the presence and absence of 20 µM oligomycin. The results are the means of two experiments which did not vary more than 10%.

These results are consistent with the heterologous expression of a nucleotide triphosphatase activity with the characteristics expected for a Pdr5p homologue. They provide the first reliable measurement of the in vitro activity of Cdr1p. Crd1p is not sufficiently prominent in assays with *C. albicans* plasma membranes to be discriminated from the activities of other ATP utilising enzymes such as the plasma membrane proton pump and endogenous members of the ABC-transporter family. The nucleotide triphosphatase activity in plasma membranes from AD1002 is sufficient to determine several of the biochemical characteristics of the enzyme and for it to be used in the screening for, or the assay of, agonists or antagonists that may be candidates for drug discovery purposes.

Parallel studies indicate that the present invention can be more broadly applied. The *C. albicans* CDR2 gene is a homologue of CDR1. The *C. albicans* CDR2 ORF was cloned into the pSK-PDR5PPUS vector and used to transform AD1-8u$^-$.

A resultant Ura⁺ transformant, with the CDR2 ORF integrated into the PDR5 locus, was resistant to fluconazole (MIC=64 µg/ml, Table 2) and was cross-resistant to ketoconazole (2 µg/ml) and itraconazole (1 µg/ml) (Table 2). DNA sequence analysis of PCR products obtained from the genomic DNA of the transformant showed that the coding region in the transformed PDR5 locus was identical to that of the CDR2 in the genome of the donor strain ATCC 10261. Northern analysis showed that the CDR2 mRNA was highly expressed in the transformant. Gel electrophoresis of purified plasma membranes from the transformant revealed the presence of a major 170 kDa band in amounts comparable to the endogenous levels of the 100 kDa Pma1p band. In a further study the ORFs of the *Candida glabrata* CDR1 and PDH1 genes, which are related to *S. cerevisiae* PDR5, were transformed into the PDR5 locus of strain AD1-8u⁻. These constructs, gave genomic DNA sequences in the PDR5 locus that were identical to the coding sequence of *C. glabrata* CDR1 and PDH1, respectively. Both constructs expressed the produced expected heterologous mRNA, hyper-expressed the expected protein product in plasma membrane fractions (identified by internal sequence analysis of the proteolytically digested gel band), conferred resistance to azole and triazole drugs but not polyene antibiotics. Under glucose-energised conditions, these strains effluxed the ABC-transporter substrate rhodamine 6G at high rates while a null mutant failed to efflux rhodamine 6G. Both hyper-expressed proteins could be shown to be phosphorylated in vivo. These results show that the present invention can allow high fidelity cloning and confirms the ability to achieve heterologous functional hyper-expression of plasma membrane proteins, in particular proteins of the ABC-transporter class, in *S. cerevisiae*.

Example 3

The Heterologous Hyper-Expression of Different Classes of Membrane Protein and Its Application to Drug Discovery Materials and Methods
Preparation of Transformation Cassettes in pABC3

Pfx DNA polymerase (Gibco BRL, Life Technologies, Rockville, Md.) was used to PCR amplify CDR1, BEN^R and ERG11 from *C. albicans* ATCC 10261 genomic DNA and PDR5 from *S. cerevisiae* AD124567 using primers containing PacI or NotI restriction sites: The primers pairs, with relevant restriction sites underlined, were:

1. CDR1,
5'-GTCAAAATTAATTAAAAAATGTCAGATTCTAAG  (SEQ ID NO:
ATGTCGTCGCAA-G-3'                   8)
and 5'-ACGCGGCCGCTTAGTGATGGTGATGGTGATGTT  (SEQ ID NO:
TCTTATTTTTTTTCTCTCTGTTACCC-3'       9)

2. BEN^R,
5'-CATCTACTTACATTAATTAACACAATGCATTA  (SEQ ID NO:
CAG-3'                              10)
and 5'-GGAAAACAATGCGGCCGCCTAATTAGCATA-3'  (SEQ ID NO:
                                     11)

3. ERG11,
5'-TTCAAGAAGATTAATTAACAATATGGCTATTGT  (SEQ ID NO:
TGAAACTG-3'                         12)
and 5'-GAATCGAAAGAAAGCGGCCGCTTTATTAAAACA  (SEQ ID NO:
TACAAGTTT-3',                       13)

4. PDR5,
5'-GTTTTCGTGGCCGCTCGGGCCAAAGACTTAATT  (SEQ ID NO:
AAAAAATGCCCGAGGC-3'                 14)
and 5'-ACCCACATATAGCGGCCGCATATGAGAA       (SEQ ID NO:
GACG-3'.                            15)

Each PCR product was digested with PacI and NotI and cloned into plasmid pABC3 that had been predigested with PacI and NotI. The orientation of each open reading frame (ORF) was confirmed by sequencing to be the same as PDR5. Each plasmid was digested with AscI and used to transform *S. cerevisiae* AD1-8u⁻ to Ura⁺ by the lithium acetate transformation protocol (Alkali-Cation Yeast kit, Bio-101).

Disk Drug Susceptibility Assays.

Drug susceptibility was measured using disk assays on CSM-URA plates (containing 1.5% w/v agar). Yeast cells (200 µl ml of 5×10⁶ cells/ml) were spread on the plates. 10 µl of drug solution or solvent control were spotted onto sterile Whatman paper disks on the pre-spread plates. The following amounts (nmoles) of drugs were applied to individual disks: fluconazole, 633 (Pfizer Ltd., Sandwich, Kent, United Kingdom); itraconazole, 0.23 (Janssen); miconazole, 0.42 (Janssen); cycloheximide, 0.71 (Sigma); rhodamine 6G, 100 (Sigma, Penrose, Auckland, N. Z.); rhodamine 123, 125 (Sigma); cerulenin 4.5 (Sigma); 5-flucytosine 100 (Sigma); amphotericin B, 97 (E. R. Squibb & Sons, Princeton, N.J.); nystatin 65 (Sigma). Agar plates were incubated at 30° C. for 48 h or until clear growth inhibition zones were visible.

Results

The discovery of a system that functionally hyper-expresses different classes of membrane protein in the plasma membrane of *S. cerevisiae* has major implications for the genetic, physiological, biochemical and structural study of such molecules. It opens important avenues for practical application in areas such as drug discovery and biosensing. For example, membrane proteins constitute a high percentage of cellular proteins and they also contribute the major proportion of existing drug targets, while many biosensors use membrane proteins as receptors or as components of receptor-linked systems in signaling processes. The previous two sections of this document showed the functional heterologous hyper-expression of the *C. albicans* Cdr1p ABC transporter and noted the hyper-expression of related transporters from *C. albicans* (Cdr2p) and *C. glabrata* (Cdr1p and Pdh1p). This was achieved by expressing these foreign ABC transporter genes, integrated at the PDR5 locus in the *S. cerevisiae* AD1-8u⁻ strain, under control of the pdr1-3 gain of function mutation in the Pdr1p transcriptional regulator. The present section provides examples of the broader applicability of this system to further classes of membrane proteins. It uses, as an illustrative example, the functional heterologous hyper-expression of representatives of three distinct classes of membrane proteins from *C. albicans* that are responsible for determining three separate modes of resistance to the antifungal drug fluconazole. In particular, it demonstrates and compares the functional hyper-expression, based on the AD1-8u⁻ host strain, of Ben^Rp, Erg11p and separate alleles of Cdr1p. The vector used to prepare the transformation cassettes for these studies was pABC3 (FIG. 1B). For these studies strain AD1-8u⁻ and strain AD-pABC3 (AD1-8u⁻ transformed with the unmodified transformation cassette from pABC3) were used as negative controls for pump expression (FIG. 7, lanes 7 and 2 respectively). Strain AD-PDR5, prepared with a transformation cassette that included the complete *S. cerevisiae* PDR5 ORF (FIG. 7, lane 3), served as a positive control for pump expression. FIG. 7 shows the Coomassie blue R250-stained protein profiles of plasma membranes obtained from these control strains and the engineered strains AD-CDR1 (lane 4), AD-ERG11 (lane 5), and AD-BEN$^R$ (lane 6). The last three strains were obtained by homologous recombination using transformation cassettes containing the *C. albicans* CDR1, BEN$^R$ and ERG11 ORFs, respectively. See Materials and methods for the preparation of the transformation cassettes. While AD-BEN$^R$ and AD-ERG11 were constructed in strain AD1-8u, AD-CDR1 was constructed in the temperature sensitive strain AD1-8u⁻ sec6-4. As expected, the AD-CDR1 strain was temperature sensitive when grown at 37° C. When grown at the permissive temperature of 30° C. plasma membranes from strain AD-CDR1 showed the presence of a major 170 kDa protein band that was not found in either of the two negative control strains. This band was detected in an amount that was at least 2-fold in excess of the endogenous 100 kDa Pma1p band and was comparable with the amount of Pdr5p found in membranes from strain AD-PDR5, in which the Pma1p and Pdr5p bands were present in equivalent amounts (FIG. 7 compare lanes 3 and 4). We have noted, in some instances, that hyper-expression of ABC-transporters gives up to a 50% decrease in the amount of Pma1p found in the plasma membrane fraction compared with the control AD1-8u⁻ strain. This decrease is not accounted for by the increased contribution of the heterologously expressed band to the plasma membrane fraction. Based on these considerations the Cdr1p band contributes at least 10-20% of plasma membrane protein in strain AD-CDR1. SDS-PAGE analysis of plasma membranes from the AD-ERG11 construct (FIG. 7 lane 5) showed the presence of a protein band at about 61 kDa that that was stained to about half the intensity of Pma1p and was not found in any of the control strains. Assuming equivalent Coomassie blue staining per unit mass of protein, this result indicates the detection of approximately equal numbers of Pma1p and Erg11p molecules in plasma membranes from this strain. However, the AD-ERG11 membranes gave no indication of an additional protein band that might correlate with the 680 amino acid Prd1p, the NADPH-cytochrome P-450 reductase that is required for the catalytic function of Erg11p. The enzyme lanosterol 14α-demethylase encoded by ERG11 is a member of the family of cytochrome P-450 enzymes. This enzyme is normally located in the endoplasmic reticulum. Comparative cell fractionation studies with strains AD-pABC and AD-ERG11 show that while a 61 kDa band specific to the AD-ERG11 strain was detectable in microsomal fractions obtained by differential centrifugation, the plasma membranes fraction (marked by the 100 kDa Pma1p band) showed several-fold higher levels of the 61 kDa band (data not shown). This indicates that hyper-expression targets excess of lanosterol 14α-demethylase to the plasma membrane, possibly via a default pathway. Finally, the plasma membrane fraction from the AD-BEN$^R$ strain (FIG. 7 lane 6) showed the presence of a slightly fuzzy protein band at 60 kDa corresponding to the molecular size expected for Ben$^R$p. It was present in amounts approximately equivalent to the Pma1p band, was detected immunochemically with an antibody directed against recombinant Ben$^R$p antigen, and was not present in the control strains (compare with lanes 2 and 7). These results indicate that the AD-BEN$^R$ strain may insert more Ben$^R$p than Pma1p molecules into the plasma membrane.

Disk diffusion assays, which used the AD-pABC construct as negative control, demonstrated the response of each hyper-expressing construct to individual toxic antifungal agents and to separate classes of these molecules (FIG. 8). Differential resistance/sensitivity profiles were obtained that reflected the functional hyper-expression and known specificity of each recombinant membrane protein. Strains AD-PDR5, AD-CDR1, AD-BEN$^R$ and AD-ERG11 showed differential sensitivities to fluconazole that were confirmed by the determination of MICs in liquid microdilution assays. Strains AD-PDR5, AD-CDR1, AD-BEN$^R$ and AD-ERG11 had MICs of 400, 400, 80 and 2 ug/ml fluconazole respectively, compared with AD-pABC3 which had an MIC of 0.5 ug/ml fluconazole. AD-PDR5 and AD-CDR1 showed identical resistances to the triazole (fluconazole and itraconazole) and azole (miconazole) drugs, and to cycloheximide, rhodamine 6G and rhodamine 123, as expected for the broad specificity of the ABC-transporters Pdr5p and Cdr1p. The expected sensitivities of AD-PDR5 and AD-CDR1 to flucytosine (5-FC) and to the polyene antibiotics amphotericin B and nystatin were confirmed in the disk diffusion assays. The compound 5-FC targets the enzyme thymidylate synthase and the polyene antibiotics target membrane ergosterol, respectively, and are not known as ABC-transporter substrates. The same assays with AD-BEN$^R$ showed that the hyper-expressed Ben$^R$p transporter had narrower substrate specificity. Thus, AD-BEN$^R$ was resistant to the Ben$^R$p substrates fluconazole, cycloheximide and cerulenin, it showed detectable resistance to miconazole, but was fully sensitive to the ABC-transporter substrates rhodamine 6G, rhodamine 123 and itraconazole, which are not known as substrates of Ben$^R$p. As expected AD-BEN$^R$ was sensitive to 5-FC and the polyene antibiotics. AD-ERG11, in line with its ability to confer modest resistance to fluconazole, also showed some resistance to both itraconazole and miconazole, as would be expected of the hyper-expression of their common target lanosterol 14α-demethylase. AD-ERG11 was also susceptible to the drug efflux substrates cycloheximide, cerulenin, rhodamine 6G and rhodamine 123, the antifungal 5-FC and both polyene antibiotics tested.

The hyper-expression of Cdr1p, Ben$^R$p and Erg11p in the fluconazole sensitive AD1-8u⁻ background demonstrates unambiguously both function and specificity for three different classes of membrane proteins which confer fluconazole resistance through separate mechanisms.

Many pathogenic fungi, including *C. albicans, C. tropicalis, C. krusei* (but not *C. glabrata*), are diploid organisms. The membrane protein hyper-expression system provides a test for functional differences between alleles because it allows individual alleles to be selectively amplified and their phenotypes compared in a defined host deleted of confounding background factors. Sequencing of genomic DNA amplified by PCR has identified several single nucleotide polymorphisms (SNPs) in the CDR1 gene of *C. albicans* strain AD10261 that predict amino acid differences between the gene products (data not shown). We have therefore, as an example, separately hyper-expressed each allele of *C. albicans* CDR1 in *S. cerevisiae* AD1-8u⁻. The two 170 kDa Cdr1ps were detected in equivalent amounts in plasma membrane preparations analysed by SDS-PAGE and the constructs showed differential resistance to fluconazole. Allele 1 (CDR1-1) obtained from strain ATCC10261 appears identical to both the published sequence for cloned CDR1 (cloned in strain JG436, Prasad R, et al, 1995) and the sequence available from the *C. albicans* genome sequencing project (Strain SC5314). Hyper-expression of CDR1-1 gives an MIC=400 μg/ml for fluconazole. Hyper-expression of the second allele (CDR1-2) confers an MIC=80 ug/ml for fluconazole.

The impact of individual gene alleles on fungal disease is poorly understood. The ability to demonstrate clear cut functional differences between alleles differentiated by SNPs, by magnifying their expression in a minimized background, provides a tool to investigate whether SNPs affect the evolution of drug resistance through mechanism such as, but not restricted to, mitotic gene recombination. For example, mutations or other genetic events that cause the high level expression of a more drug resistant allele could render existing drugs like fluconazole ineffective. More generally, the yeast membrane protein hyper-expression system of the invention may be of value in expressing targets, drug processing enzymes, or molecules affected by mechanism-based toxicity, such as closely-related or SNP-affected genes encoded by microbial pathogens, fungi, plants, animals or humans. The system could be used to select for drugs which are fully effective against pathogens or to tailor medications which take into account pharmacogenomic differences within individual species or between patients.

The ability to functionally hyper-express individual membrane proteins in S. cerevisiae can give rise to selectable phenotypes such as drug resistance. This is exemplified by the selection of fluconazole resistant phenotypes resulting from the expression of versions of multidrug efflux pumps from the PDR5 locus in AD1-8u⁻. These phenotypes give susceptibilities, ranging from <10 µg/ml to 100s of µg/ml of fluconazole, and occur for a variety of reasons. These include, but are not limited to, constructs which restrict expression from the PDR5 locus, constructs which have partially or fully compromised function because of mutations in the coding region, or because a partial version of a foreign gene has been integrated into the PDR5 locus as an interim measure designed to circumvent the toxicity that can be associated with the cloning of genes specifying membrane proteins in E. coli when using plasmids such as pSK-PDR5PPUS and its derivatives.

The following examples demonstrate that linear DNA sequences can be used to complement such defects, with the corrected phenotype obtained by selection for a higher level of drug resistance. FIG. 9 shows a construct containing an SfiI site immediately upstream of the PacI site in the pABC3 transformation cassette led to dramatically lower functional expression of Pdr5p. The limitation on expression in this system is directly attributed to the presence of the SfiI site and not the PacI site, because the PacI site alone had no effect on the functional expression of Pdr5p from this locus (compare FIG. 9, lanes 2-6). The engineered protein expressed from SfiI-containing constructs was barely detectable in SDS-PAGE separated plasma membrane preparations and the construct showed low fluconazole resistance (MIC<40 mu.g/ml). A similar defect in an AD1-8u.sup.-strain engineered to express Cdr1p could be corrected by transformation with a linear DNA PCR fragment encompassing 350 nucleotides of the promoter region and 360 nucleotides of the CDR1 coding region from plasmid pKEN1002. The PCR product was amplified using the primers 5'-ATCACGATTCAGCAC-CTTT-3' (SEQ ID NO: 16) and 5'-CCCAAAATTTGGCAT-TGAAA-3' (SEQ ID NO: 17). Transformants were selected on a solid CSM medium that contained 40 mu.g/ml fluconazole plus 2% glycerol and 0.1% glucose as an energy sources. This combination of energy sources was used to identify and select against respiratory incompetent petite yeast that can show enhanced fluconazole resistance. The initial construct in AD1-8u⁻ had barely detectable expression of Cdr1p and an MIC for fluconazole of 20 ug/ml. The selected respiratory competent construct gave isolates with an MIC for fluconazole of 400 ug/ml and Cdr1p was expressed in plasma membranes in amounts comparable to that found in AD1002. In another example, successive attempts to clone the PDH1 gene of C. glabrata into the multicloning site of pSK-PDR5PPUS plasmid failed, possibly due to lethality in E. coli. As an alternative strategy nucleotides 1-530 and nucleotides 4532-5486 of PDH1 were cloned into the HindIII/EcoRI and the XmaI/SpeI sites of pSK-PDR5PPUS vector, respectively, and the resultant KpnI-NotI transformation cassette used to transform the AD1-8u⁻ PDR5 locus by homologous recombination, conferring uracil auxotrophy but retaining full sensitivity to fluconazole. A PCR fragment comprising nucleotides 1-5342 of PDH1 was obtained by amplification of genomic DNA and used to transform the AD1-8u⁻ derivative host strain containing the flanking PDH1 fragments to fluconazole resistance (MIC=200 ug/ml). The resultant construct contained a coding region identical to that of genomic PDH1 and its 170 kDa protein product was functionally hyper-expressed in the plasma membrane of the S. cerevisiae host strain (data not shown).

More generally, the ability to select more resistant phenotypes has many applications. These include, but are not limited to, the ability to modulate levels of functional protein expressed from the PDR5 locus, the transformation of the S. cerevisiae PDR5 locus with genes that may be difficult to clone in E. coli, the creation of chimeric molecules and the complementation of drug sensitive phenotypes that may be generated by site-directed mutagenesis and other genetic manipulations. With the ability to hyper-express different classes of proteins from the PDR5 locus, forms of selection other than the acquisition of fluconazole resistance are also readily envisaged.

Example 4

Application of Functional Heterologous Hyper-Expression of Membrane Proteins to Drug Discovery Materials and Methods Yeast Strains In addition to the yeast strains described in the previous Materials and methods section, S. cerevisiae strain AD1234567 (MATα, pdr1-3, his1, Δyor1::hisG, Δsnq2::hisG, Δpdr5::hisG Δpdr10::hisG, Δpdr11::hisG, Δycf1::hisG, Δpdr3::hisG [Decottignies, A. et al, 1998]) was used.

Checkerboard Drug Susceptibility Assays.

Checkerboard drug susceptibility assays were used to measure the chemosensitisation of cells to fluconazole by test compounds such as Pdr5p inhibitors. Fluconazole concentration in the CSM-URA medium was varied in one dimension (between 0 and 80 µg/ml) and the concentration of the test compound was varied in the second dimension (between 0 and 40 µM). Cell inocula, growth conditions and the optical determination of growth were identical to standard liquid MIC determinations. The assays were conducted in 6 by 6 well arrays centred in a 96 well microtitre plate using buffered CSM-URA medium at pH 7.0, with fluconazole and/or peptide included in each well at the indicated concentration. Growth yields were measured after 48 h incubation at 30° C. and all data were tabulated, calculated and displayed using Microsoft EXCEL software.

Fluconazole Accumulation by S. cerevisiae Cells.

The net rate of fluconazole accumulation by early exponential phase S. cerevisiae cells was measured as previously described (Albertson, G. et al, 1996). To examine the energy-dependence of fluconazole accumulation, assays contained 20 mM sodium azide.

Disk Diffusion Assays.

These assays were conducted as described in example 2. Where indicated, disk assays were conducted with agarose in the place of agar. This is required to observe effects with peptide inhibitors of Pdr5p, which may otherwise absorb to agar constituents.

Rhodamine 6G Efflux and the Characterisation of Inhibitors of Cdr1p Function.

A previously described method (Kolaczkowski, M et al. 1996) was adapted to measure rhodamine 6G (Sigma) efflux from whole cells. Yeast cells from exponentially growing cultures in YEPD ($OD_{600\,nm}$=0.5) were collected by centrifugation (3,000×g, 5 min, 20° C.) and washed three times with water. The washed cells were resuspended at a concentration of $0.5 \times 10^6$ to $1.0 \times 10^7$ cells per ml in HEPES-NaOH (50 mM, pH 7.0) containing 5 mM 2-deoxyglucose and 10 µM rhodamine 6G. In some experiments fluconazole (10 µM) was also added. Cell suspensions were incubated at 30° C. with shaking for 90 min to allow rhodamine accumulation under glucose starvation conditions. The starved cells were washed twice in 50 mM HEPES-NaOH pH 7.0, and portions (400 µl) incubated at 30° C. for 5 min before addition of glucose (final concentration 2 mM) to initiate rhodamine efflux. At specified intervals after the addition of glucose, cells were removed by centrifugation, and triplicate 100 µl volumes of the cell supernatants transferred to wells of 96 well flat-bottom microtitre plates (Nunc, Roskilde, D K). The rhodamine 6G fluorescence of samples was measured using a Cary Eclipse spectrofluorimeter (Varian Inc, Victora Australia). The excitation wavelength was 529 nm (slit 5) and the emission wavelength was 553 nm (slit 10). In some experiments fluconazole at 10 µg/ml was included in all steps of the assays, while in other experiments peptides at the indicated concentration were added to the assay at the beginning of the 5 minute incubation at 30° C. prior to the addition of glucose.

Results

The utility of the Cdr1p over-expressing strain AD1002 and other strains over-expressing membrane proteins for drug discovery purposes is illustrated.

Figure 10A:
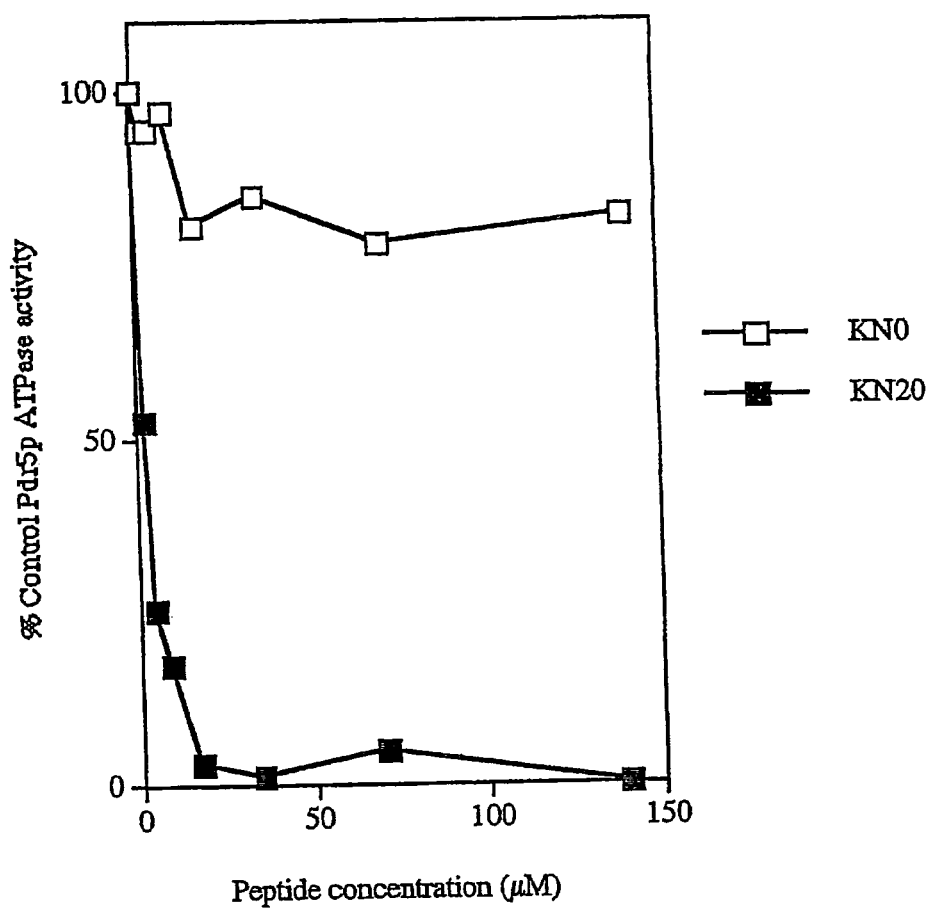
Figure 10B:
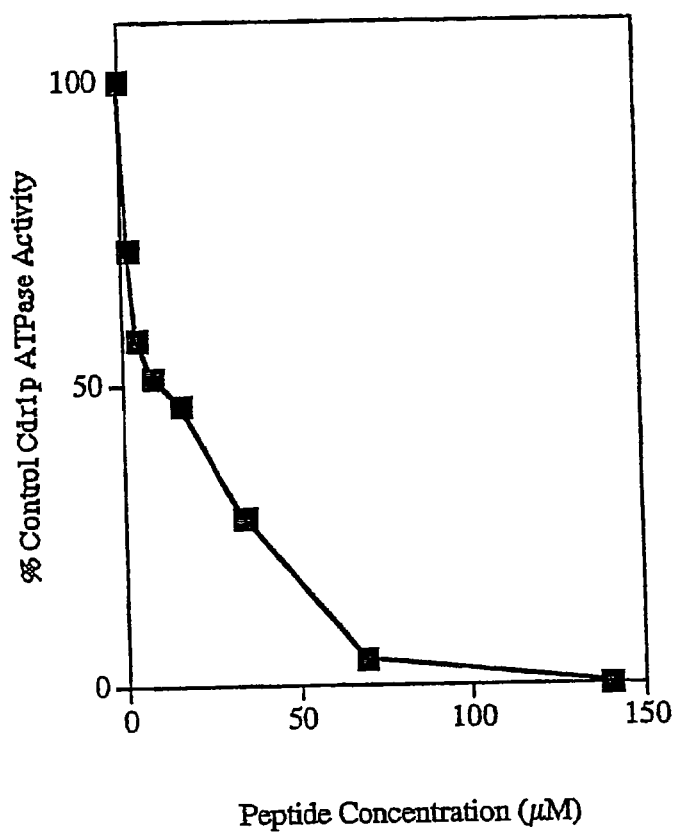
Figure 11A:
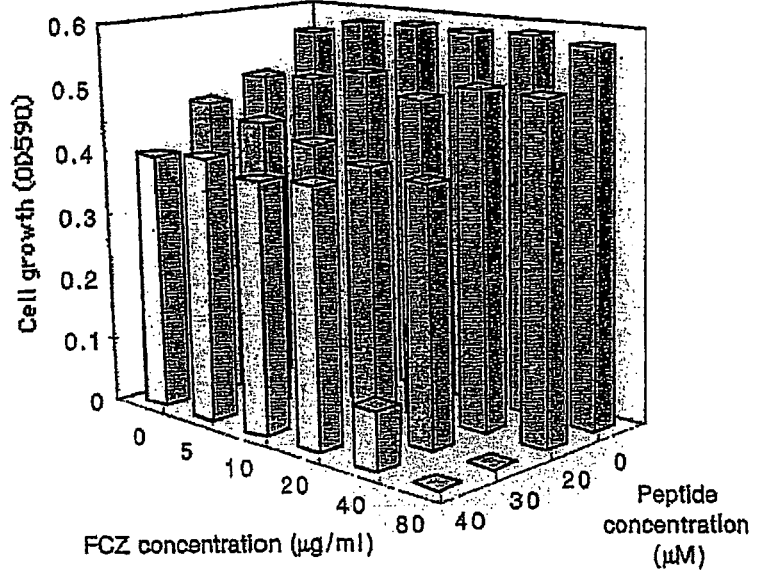
Figure 11B:
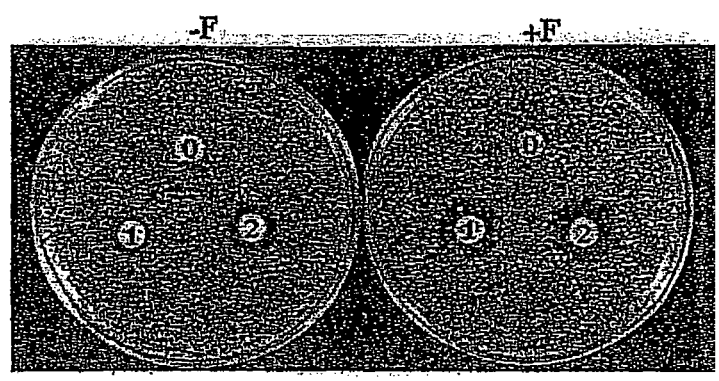

FIG. 10A shows the effect of two purified peptides on oligomycin sensitive Pdr5p ATPase activity. The compound denoted KN20 is a Pdr5p inhibitor with the primary structure D-NH$_2$-asparagine-tryptophan-tryptophan-lysine-valine-arginine-arginine-arginine-CONH$_2$. KN20 has a further essential element in the form of a single 4-methoxy-2,3,6-trimethylbenzenesulphonyl substituent linked to of either one of the tryptophan sidechains, possibly via the nitrogen or the adjacent carbon {C2} of the indole ring, although other modes of attachment to the peptide may be possible. KN20 inhibited the oligomycin sensitive ATPase activity of plasma membranes from the AD124567 yeast strain overexpressing Pdr5p with an I50 of about 3 µM at pH 7.5 (FIG. 10A) while the purified non-derivatised peptide was ineffective. KN20 also inhibited the oligomycin sensitive ATPase activity of AD1002 plasma membranes with an I50 of about 8 µM. (FIG. 10B). The inhibition of the Cdr1p ATPase at only 2.7-fold higher concentrations than the Pdr5p ATPase indicated that KN20 could be developed as a broad-spectrum inhibitor of multidrug resistance caused by fungal ABC-transporters. Checkerboard drug susceptibility assays conducted at pH 7.0 demonstrated that 30 µM KN20 chemosensitised the Pdr5p overexpressing yeast strain to a sub-MIC concentration (80 µM) of fluconazole (FIG. 11A). Disk drug susceptibility assays (FIG. 11B) visually demonstrated the chemosensitisation of the Pdr5p-overexpressing AD124567 strain to 120 µg/ml fluconazole by amounts of peptide which by themselves have little or no effect on the overall growth of the yeast. In contrast, KN0 (which is identical to KN20 but lacks the Mtr substituent) was ineffective at chemosensitisation at these concentrations.

Figure 12A:
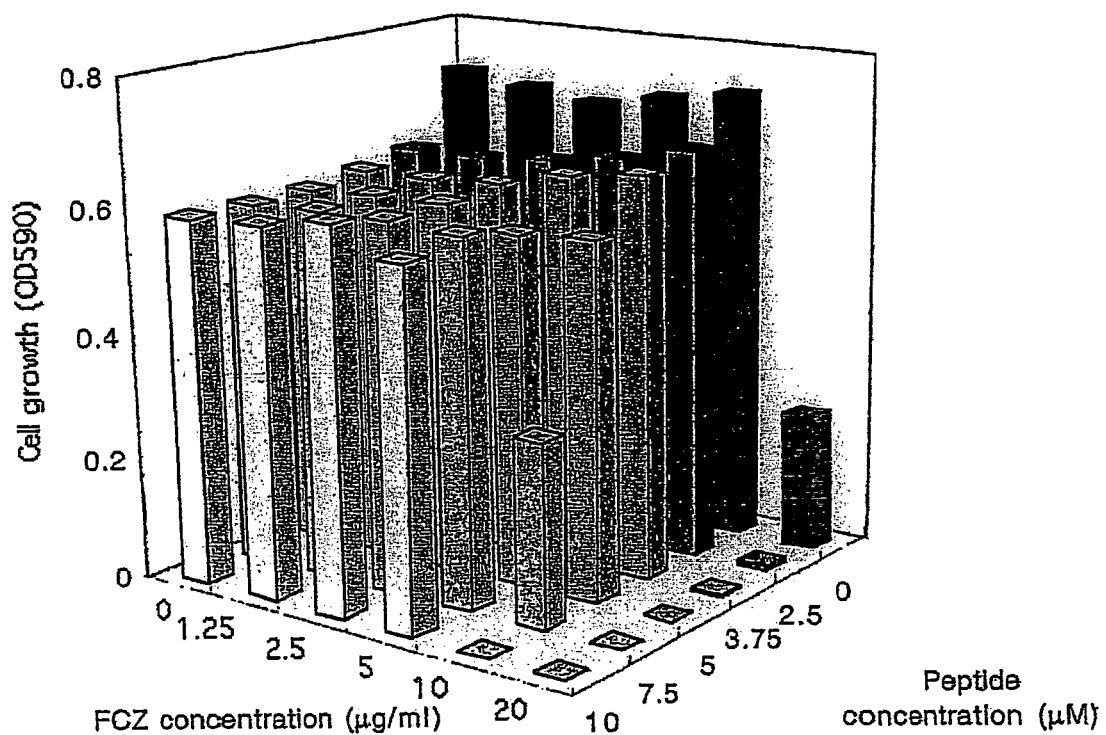
Figure 12B:
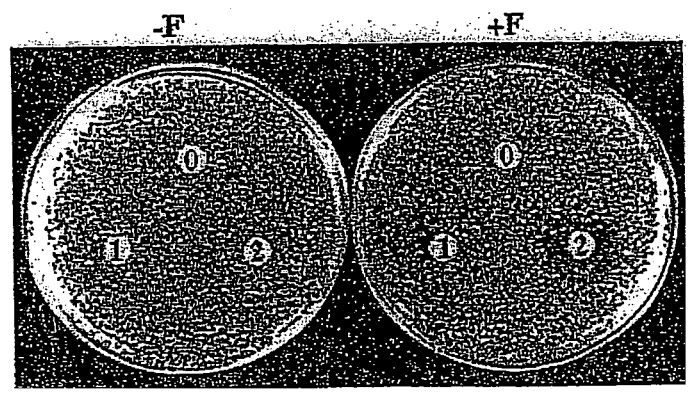

AD1002 cells grown in buffered CSM-URA medium at pH 7.0 containing the drug fluconazole gave a fluconazole MIC of 30 µg/ml (Table 2). In the same medium but without fluconazole, the cells were completely resistant to 10 µM KN20 and the peptide alone at 20 µM did not affect overall growth after 48 h (FIG. 12A). However, exposure to 10 µg/ml fluconazole plus 10 µM of KN20 completely abolished growth of the strain. This result shows that KN20 synergistically enhances fluconazole inhibition of growth in strain AD1002. We postulated that KN20 abolishes fluconazole resistance by inhibiting efflux mediated by Cdr1p. This inhibition will raise the intracellular concentration of fluconazole to the extent that ergosterol biosynthesis is inhibited and hence growth is affected. Disk drug susceptibility assays confirmed that KN20 chemosensitises AD1002 to fluconazole at KN20 concentrations that do not affect overall growth. (FIG. 12 B). In contrast, KN0 was ineffective at chemosensitisation at these concentrations.

TABLE 4

KN20 chemosensitisation of *Candida* clinical isolates and *S. cerevisiae* strains hyper-expressing individual ABC transporters.

| Yeast species | Strain (hyper-expressed transporter) | Chemosensitising concentration KN20 (µM) | FCZ (µg/ml) | Fold-sensitisation by KN20 (For FCZ MIC) |
|---|---|---|---|---|
| C. albicans | ATCC10261 | 80 | 2 | 64[a] |
| C. albicans | FR2 (Ben$^R$p) | 20 | 8 | 4 |
| C. glabrata | CBS138 | 40 | 20 | 4 |
| C. tropicalis | IFO0618 | 10 | 10 | 16[a] |
| C. krusei | B2399 | 80 | 80 | 2.5 |
| C. dubliniensis | CD36 | 80 | 0.31 | 64.5[a] |
| C. parapsilosis | 425 | 0-80 tested | 32 tested | 1[b] |
| S. cerevisiae | AD12345678u- | 7.5 | 0.125 | 2 |
|  | AD124567 (Pdr5p) | 20 | 60 | 10 |
|  | AD1002 (CaCdr1p) | 10 | 10 | 4 |
|  | 27A (CaCdr2p) | 20 | 20 | 4 |
|  | 1B (CgCdr1p) | 15 | 40 | 8 |
|  | 4 (CgPdh1p) | 20 | 1.25 | 16 |
|  | AD-BEN$^R$ (Ben$^R$p) | 20 | 3.75 | 16 |
|  | AD-ERG11 (Erg11p) | 20 | 0.25 | 8 |

[a]Resistant "tail" eliminated;
[b]No chemosensitisation

Figure 12C:
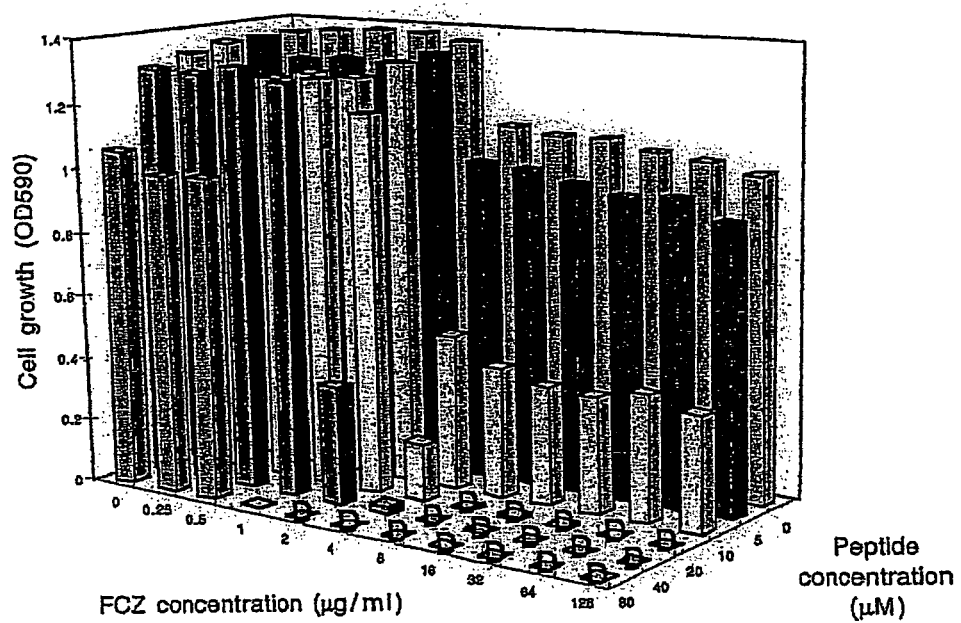

KN20 chemosensitisation of AD1002 to fluconazole shows that this strain can be used to select and/or characterise inhibitors of Cdr1p-dependent multidrug efflux. FIG. 12C and Table 4 shows that KN20 also chemosensitises the tail of low level resistance seen with populations of wild type *C. albicans*, as exemplified by drug susceptibility assays of strain ATCC 10261. This low level resistance type is commonly seen in *C. albicans* strains and may be important for the subsequent evolution of the intermediate level resistance found in clinical isolates obtained after long term prophylactic exposure to fluconazole. KN20 also chemosensitises the intrinsically fluconazole-resistant *Candida glabrata* strain CBS138 and the *Candida krusei* strain B2399, as well as clinical isolates of the pathogens *Candida tropicalis*, and *Candida dubliniensis* (Table 4). However it did not chemosensitise *C. parapsilosis* strain 425. These results suggest that inhibitors like KN20 may find quite broad application to the inhibition of multidrug efflux mediated by pumps related to Pdr5p and Cdr1p.

The present invention provides a system to gauge the breadth of action of inhibitors like KN20, independent of limitations imposed by the genetic backgrounds of the organisms donating the DNA encoding the targets. For example, the over-expression of other potential targets such as Cdr2p or individual ABC-transporters from other organisms in the AD1-8u-background provides assays to measure the effect of KN20 on the functioning of these targets. Table 4 shows that each ABC-transporter construct tested was chemosensitised to fluconazole by sub-MIC concentrations of KN20.

Figure 13A:
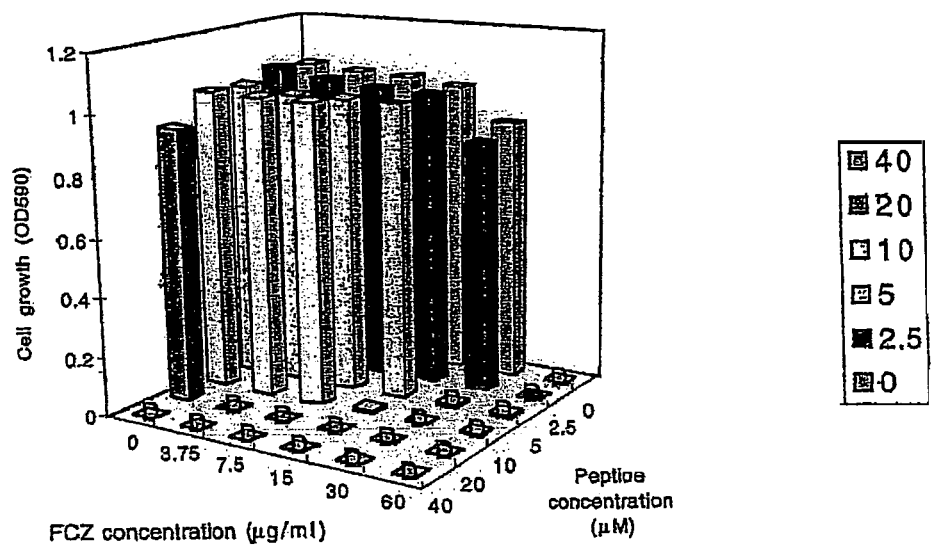
Figure 13B:
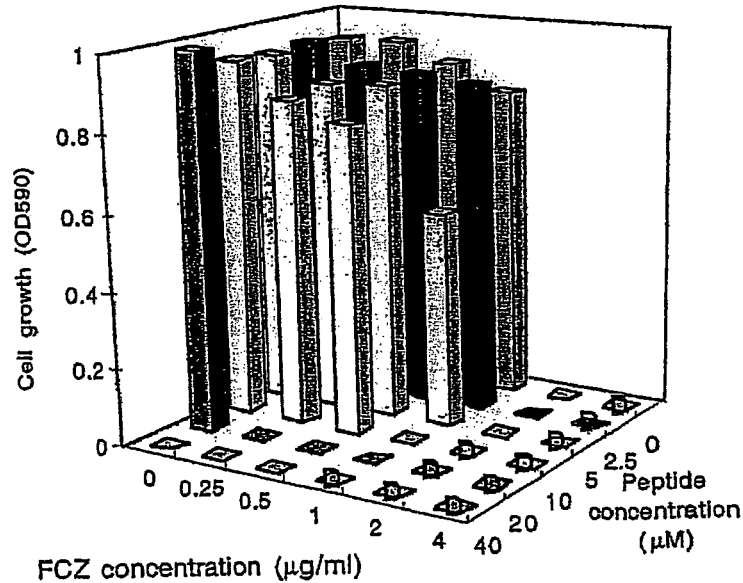

The present invention also provides a system to test other aspects of specificity for inhibitors like KN20. For example, KN20 might be expected to chemosensitise fluconazole resistant *C. albicans* clinical isolates that specifically over-express Cdr1p but not strains that rely on the over-expression of a Major Facilitator Superfamily Transporter $Ben^Rp$. However, clinical isolates of *C. albicans* are genetically diverse and the molecular basis of fluconazole resistance is often multifactoral (Albertson et al, 1996). Drug resistance in *C. albicans* can involve expression of various combinations Erg11p, Cdr1p and $Ben^Rp$, as well as unrelated molecules, thereby complicating understanding of the role of specific molecules in the causation of resistance and in interpreting the effects of specific inhibitors. These problems mean that clinical isolates will often be inappropriate experimental models for mode of action studies. For example, the fluconazole resistant *C. albicans* FR2 strain, which has been shown to over-express $BEN^R$, was chemosensitised by KN20 (Table 4). This suggested but did not prove that KN20 affected a target other than its ABC-transporters. This problem has been overcome by over-expressing functional $Ben^Rp$ in strain AD1-8u⁻. The resultant isogenic construct, strain AD-$BEN^R$, allows a valid test of the hypothesis that chemosensitisation by KN20 is directly mediated by inhibition of Cdr1p. In particular, a fluconazole resistant AD-$BEN^R$ strain should not be chemosensitised by KN20 or any other specific chemosensitisers of Cdr1p. Conversely, chemosensiters which act directly and specifically on $Ben^Rp$ should not chemosensitise the AD1002 strain or other strains which functionally over-express Cdr1p or Cdr2p in the AD1-8 background. As shown in FIG. 13A and summarized in Table 4, *C. albicans* $Ben^Rp$ functionally hyper-expressed in strain AD1-8u⁻ is chemosensitised by KN20. This indicates that KN20 has a different target from Cdr1p in whole cells. KN20 also chemosensitises strain AD-ERG11 to fluconazole (FIG. 13B and Table 4). These data indicate that a target other than Cdr1p may be the primary site of action of KN20 in cell-based assays. The fungal plasma membrane H⁺-ATPase is the primary pump that generates the plasma membrane electrochemical gradients which drive the $Ben^Rp$ pump and the uptake of nutrients needed for the generation of cellular energy currency (ATP and NADPH) needed by the ABC-transporters and lanosterol 14α-demethylase. The *S. cerevisiae* plasma membrane H⁺-ATPase is inhibited by KN20 (150=10 μM). Concentrations of KN20 of 10 μM or greater are required to chemosensitise *S. cerevisiae* cells hyper-expressing Pdr5p, Cdr1p and $Ben^Rp$ (Table 4). These data and in house studies with Pma1p inhibitors provide strong circumstantial evidence that KN20 indirectly chemosensitises multidrug efflux via inhibition of Pma1p.

More generally, a person skilled in the art could apply versions of the MIC, checkerboard and disk drug susceptibility assays to *S. cerevisiae* strains over-expressing particular target plasma membrane proteins from a variety of organisms and perhaps enzymatic studies that might be afforded by target over-expression. These assays could be used to screen for and assess the potency and specificity of agonists or antagonists of the target molecule in a way that is not compromised by strain backgrounds. Such an investigator may also use inhibitors with a defined mode of action to investigate, for example, the nature of the efflux mediated by a particular drug pump.

Fluconazole Accumulation by AD1002.

The accumulation of [³H]fluconazole by *S. cerevisiae* AD1-8u⁻ and the transformants AD1002 and AD/pSK-PDR5PPUS was measured (FIG. 14). Energized AD1-8u⁻ or AD/pSK-PDR5PPUS cells accumulated fluconazole over a 15 min timecourse, whereas AD1002 cells did not. Addition of the respiratory chain inhibitor sodium azide to the assay had no effect on the accumulation of fluconazole by AD1-8u⁻ or AD/pSK-PDR5PPUS cells, but greatly increased accumulation by AD1002 cells. These results were consistent with the multiple drug resistance of AD1002 cells being due to energy-dependent drug efflux, and indicated that the over-expressed ABC-type transporter Cdr1p functioned as expected. An investigator skilled in the art could develop this method to screen for agonists and antagonists of multidrug efflux and to assess the physiological properties of this process.

*C. albicans* Cdr1p Mediated Rhodamine Efflux

Over-expression of Cdr1p by strain AD1002 confers the ability to pump the fluorescent substrate rhodamine 6G from cells into the medium. Rhodamine 6G has previously been demonstrated to be a substrate of Pdr5p and Yor1p and is dependent on cellular energisation (the provision of intracellular ATP through glucose fermentation). The AD1002 strain, from which Yor1p has been deleted, can be used to demonstrate competition with rhodamine 6G by other Pdr5p substrates such as fluconazole.

Figure 15A:
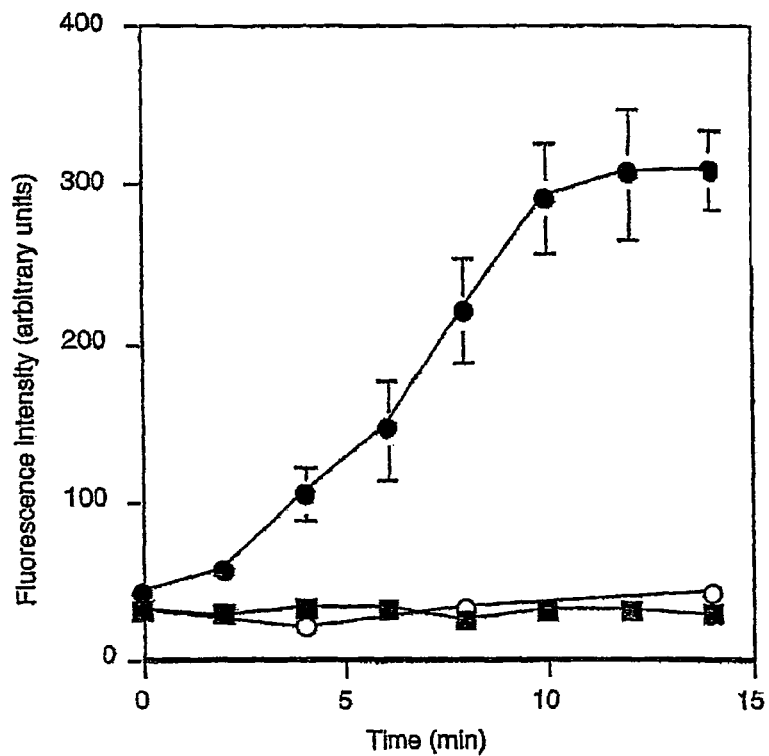
Figure 15B:
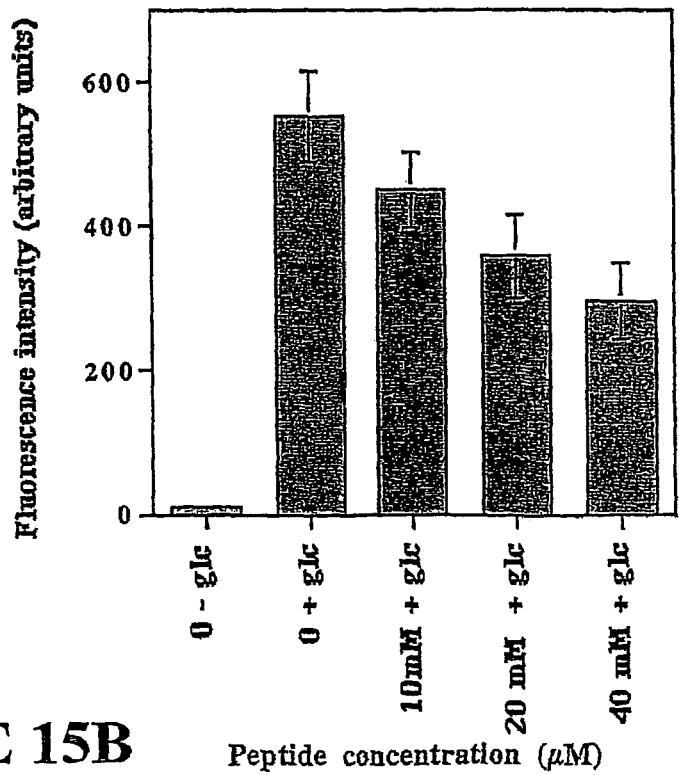

As with strain AD1234567 and AD124567 (data not shown), glucose-dependent efflux of rhodamine 6G from *S. cerevisiae* was not detectable with strain AD1-8u⁻ but was readily observed with strain AD1002 (FIG. 15A). The efflux of rhodamine 6G from preloaded de-energised AD1-8u⁻ cells (preloaded by incubation with rhodamine 6G plus 2-deoxyglucose) did not significantly increase above background levels in the presence (FIG. 15A) or absence of glucose (data not shown). Efflux from AD1002 cells preloaded with rhodamine 6G required the addition of glucose (FIG. 15A). For AD1002 the extracellular concentration of rhodamine 6G increased from a background of 30 arbitrary units of fluorescence by about 7-fold during 10 minutes following glucose addition and occurred at a rate that was at least 30-fold greater than in the presence of 2-deoxyglucose (FIG. 15A). Both AD1-8u⁻ and AD1002 showed similar survival rates following rhodamine pre-treatment, and accumulated equivalent amounts of rhodamine 6G during pre-treatment in the presence of 2-deoxyglucose, as demonstrated by determination of fluorescence released following cell lysis. The Pdr5p substrate fluconazole inhibited rhodamine efflux from AD1002 cells. The addition of fluconazole (10 µM) during preincubation of AD1002 cells with rhodamine in the presence of 2-deoxyglucose, as well as during all subsequent steps in the assay gave a 32% reduction in the concentration of released rhodamine 6G in the 10 min following the addition of glucose (data not shown). In this instance, fluconazole is thought to be competing directly with rhodamine 6G for efflux via the Pdr5p pump. This is consistent with the observation that fluconazole does not affect the in vitro oligomycin activity of the Pdr5p or Cdr1p. FIG. 15B shows that KN20 inhibited glucose-dependent rhodamine 6G efflux by strain AD124567 in a dose-dependent fashion. A 5 minute preincubation with 40 µM KN20 resulted in 50% inhibition of rhodamine 6G efflux. These observations, although not discriminating between a direct or indirect effect on Pdr5p, demonstrate the principle that the KN20 affects a directly measurable aspect of multidrug efflux. The present invention's use of rhodamine 6G efflux assay could therefore be developed to measure the effect of inhibitors on Pdr5p and related ABC-transporters.

DISCUSSION

Strategies that seek to determine target specificity or to screen for inhibitory compounds using yeast that over-express a functional target can often be complicated by the presence of multiple related endogenous molecules with various specificities. This problem is particularly important for the study of pumping mechanisms such as those involved in multidrug efflux. Circumventing this problem by the functional over-expression of the target in a system that eliminates or minimises this undesirable background is a major advantage for structure and function studies and in drug discovery. A system for the stable, functional heterologous over-expression of a target membrane protein in a strain of S. cerevisiae depleted in the major drug-efflux pumps: Pdr5p, Yor1p, Snq2p, Ycf1p, Pdr10p, Pdr11p, and Pdr15p has been demonstrated. Although none of these endogenous pumps is essential, they confer on cells overlapping capacities to tolerate xenobiotics (Decottignies A, et al 1998, Kolaczkowski M, et al, 1996) and can therefore complicate physiological studies, biochemical analysis and the drug discovery process.

A specific example concerned the integration of the CDR1 ORF into genomic DNA. This resulted in the stable inheritance of a single copy of the gene at the locus for the S. cerevisiae homologue PDR5. Fusion of the CDR1 ORF to the PDR5 promoter in a strain expressing the mutant pdr1-3 transcriptional regulator gives high level over-expression of Cdr1p. This over-expression was demonstrated as increased CDR1 mRNA, and in the appearance of a new 170 kDa protein band accounting for 10-20% of plasma membrane protein which specifically reacted with anti-C. albicans Cdr1p antibodies. The heterologously expressed protein was functional. Its expression conferred on S. cerevisiae multidrug resistance, increased levels of plasma membrane NTPase activity, gave an energy-dependent reduction in intracellular fluconazole accumulation and enhanced energy-dependent pumping of rhodamine 6G. The drug resistance phenotype was due to the over-expression of Cdr1p and not simply the pdr1-3 mutation, as the latter mutation was also present in the hyper-sensitive parental strain AD1-8u⁻ deleted of seven endogenous transporters noted above. Related properties have been observed as a result of the over-expression of C. albicans Cdr2p and C. glabrata Cdr1p and Pdh1p pumps in the AD1-8 background and of C. albicans Cdr1p in a sec6-4 derivative of AD1-8. These observations illustrate options for the broader application of the present invention to other multidrug efflux pumps of the ABC class of transporters (see below).

The high level over-expression of Cdr1p reduced the sensitivity of AD1-8u⁻ to a variety of structurally unrelated compounds that could be pump substrates. The spectrum of compounds to which Cdr1p conferred resistance was similar to that for Pdr5p (Kolaczkowski M, et al, 1996). The present results demonstrate an effect of Cdr1p expression on drug sensitivity in the absence of seven other major transporters. If the resistance phenotype is mediated by secondary effects on other transporters, it cannot involve these seven ABC pumps. Thus, we have provided clear evidence of rhodamine 6G resistance and efflux mediated by Cdr1p in the absence of Yor1p.

Plasma membranes from the Cdr1p over-expressing strain AD1002 displayed an oligomycin-sensitive NTPase activity with biochemical properties, including pH activity profiles, similar to Pdr5p—the S. cerevisiae multidrug efflux pump related to C. albicans Cdr1p (Decottignies A, et al, 1994). The pH optimum for Cdr1p UTPase activity (pH 7.0-8.0) was significantly higher than previously reported at pH 6.5 (Krishnamurthy S, et al. 1998) using a plasmid-based expression system. Interestingly, the specific activity of Cdr1p-ATPase was 4-5 times lower than the Pdr5p-ATPase activity of the Pdr5p over-expressing strain AD124567 measured under the same conditions (unpublished data). Subsequent cloning of both alleles of CDR1 confirm that mutational changes occurred during the original cloning of the CDR1-2 allele in AD1002 which affected enzyme function. Both of the new isolates show NTPase activities in vitro that are comparable to hyper-expressed Pdr5p and both confer significantly higher resistance to fluconazole (MICs of 80 and 400 ug/ml compared with 30 µg/ml for AD1002). These observations with heterologously hyper-expressed CDR1 alleles validate the search for pump antagonists that will not only circumvent the low level trailing tail of fluconazole resistance intrinsic to many wild type strains of C. albicans and the intermediate resistance (<64 µg/ml) seen in fluconazole-resistant clinical isolates but also overcome the much higher levels of resistance that could be encountered with future isolates.

The heterologous hyper-expression (>10% of plasma membrane protein) of a functional membrane protein in S. cerevisiae has been shown for both Cdr1p and Cdr2p from C. albicans and Cdr1p and Pdh1p from C. glabrata. This suggests that the invention may be more broadly applied to the heterologous expression of ABC-transporters. The heterologous over-expression of such plasma membrane proteins in a stable manner, in the types of recipient strain described in this invention, provides targets that can be analysed and utilised in an isogenic background. This will facilitate structure and function studies of individual pumps and in the development of drugs directed against this class of molecules with the requisite specificity for pharmaceutical application. The heterologous hyper-expression of functional membrane proteins in S. cerevisiae has also been shown for Ben$^R$p and Erg11p from C. albicans, with both molecules being recovered in the plasma membrane in amounts corresponding to at least that for the yeast plasma membrane H⁺-ATPase. Again it is argued that this will facilitate a wide variety of structure and function studies and aid in the development of drugs targeting such molecules. Our data provide a precedent for suggesting that many other classes of membrane proteins could be functionally hyper-expressed in this system, providing a practical tool for approaches such as the physiological, biochemical and structural genomic study of membrane proteins. Since trafficking to the plasma membrane is thought to represent a default pathway in yeast, a wide variety of hyper-expressed membrane proteins could be recovered in this organelle, although it cannot be excluded that targeting signals might be sufficient to place hyper-expressed membrane proteins in their normally targeted organelle.

The invention may be used to discover and characterise agents which chemosensitise cells via their effects on a target protein such a plasma membrane transporter. The immunosuppressive agent cyclosporine, for example, which may interact directly with multidrug efflux transporters, potentiates the effect of fluconazole in vitro and in vivo (Marchetti O, et al, 2000; Marchetti O, et al, 2000a). This invention similarly shows that competition by the Cdr1p substrate fluconazole significantly reduced the energy-dependent efflux of rhodamine 6G by the Cdr1p overexpressing strain of S. cerevisiae. Furthermore, the lead compound KN20 has been obtained as a surface-active Pdr5p inhibitor. KN20 was found to chemosensitise the Cdr1p overexpressing strain AD1002 to fluconazole in both checkerboard and disk drug susceptibility assays, it inhibited the oligomycin-sensitive ATPase activity of plasma membranes isolated from this strain and inhibited rhodamine 6G efflux in a Pdr5p overexpressing strain in a dose-dependent manner. These results suggest that KN20 may be a lead broad-spectrum inhibitor of multidrug efflux mediated by ABC-type transporters in pathogenic yeast. The inhibitor also chemosensitises the fluconazole-resistant CBS 138 strain of *Candida glabrata* and the B2399 strain of *Candida krusei* (Table 4). Although the molecule(s) mediating fluconazole resistance in this *C. krusei* strain has yet to be elucidated, fluconazole resistance in CBS 138 appears to be primarily mediated by the CgCdr1p, a homolog of *S. cerevisiae* Pdr5p and *C. albicans* Cdr1p. In addition, KN20 abolishes the low-level tail of fluconazole resistance in wild type *C. albicans*.

KN20 and its congeners are structurally and functionally different from other previously characterised multidrug efflux inhibitors. The substituted D-octapeptide does not competitively inhibit Pdr5p nucleoside triphosphatase activity because preincubation with ATP did not modify the response of the enzyme to the inhibitor (data not shown). The inhibitor is therefore unlikely to interact with the catalytic site of the multidrug efflux pump. The three arginines in KN20 give a highly positively charged molecule at physiological pH and, based on in-house studies of related model peptides and the work of others with D-peptides (Mitchell D J et al., 2000), it is unlikely to cross the yeast plasma membrane. By elimination, KN20 probably directly affects the activity of Pdr5p or Cdr1p by interacting with cell surface features of these enzymes. While the above arguments may apply to the in vitro action of KN20, the interaction between KN20 and other surface-exposed plasma membrane molecules, in particular the Pma1p, indirectly affects the function of the multidrug efflux pumps such as Pdr5p and Cdr1p. This was demonstrated by showing chemosensitisation of the Ben$^R$p transporter hyper-expressed in the AD1-8u$^-$ background at concentrations that affect the activity of Pma1p. Whatever mechanism is involved, KN20 provides a lead for a novel class of inhibitors that may find pharmaceutical or agrochemical application as antifungal chemosensitisers. Our results also imply that surface-active reagents which chemosensitise ABC-transporter mediated multidrug efflux in pathogenic yeast may represent new classes of drugs or drug leads that can be used to increase the efficacy of antifungal agents that are substrates of multidrug efflux. This approach will have application during antifungal therapy that may be directed against both wild type and resistant clinical isolates of pathogenic fungi or in the study of model yeast systems. These chemosensitisers may also circumvent the evolution of resistance e.g. by sensitising survivors in the trailing tail seen in susceptibility testing of wild type yeast. By significantly increasing the intracellular concentration of antifungal agent, these inhibitors may help overcome antifungal resistance mediated not only by ABC-transport but also by other mechanisms. These chemosensitising inhibitors may therefore lengthen the commercial life of existing antifungals, such as fluconazole and other multidrug efflux substrates, by providing more effective formulations and subverting the impact of resistance. In addition, by making such substrates more potent, it may be possible to reduce undesirable direct side-effects on the host or minimise deleterious drug interactions.

The high level expression of specific membrane transporters in a *S. cerevisiae* strain depleted in endogenous pumps opens the possibility of studying, both in vivo and in vitro, individual molecules contributing particular pumping mechanisms and exploiting this knowledge in drug discovery. More generally, by increasing the prominence of a particular kind of functional membrane protein in a background deleted of related endogenous molecules, structure and function studies that would otherwise not be possible can be implemented. The heterologous expression system will be useful in screening for pump substrates, agonists and antagonists using oligomycin sensitive NTPase activity assays with purified plasma membranes, whole cell chemosensitization (checkerboard and disk drug susceptibility assays), fluconazole uptake and rhodamine 6G efflux assays. The invention can also be used by those skilled in the art to provide, for example, quantitative measures of chemosensitiser activity in cells and in vitro, which are of value in characterising and optimising drug candidates. More general applications for other drug targets that can be expressed using adapted forms of the invention are readily envisaged. One specific example of this would be the analysis and pharmacogenomic exploitation of closely related genes and genes that contain SNPs. Another specific example would be the use of the system to select for improved antifungals such as azole and triazole drugs that are not susceptible to drug-resistance mediated by multi-drug efflux. Furthermore, the network of genes regulated by the Pdr1-3p transcriptional regulator may assist in the functional insertion of ABC-transporters and heterologous proteins into the plasma membrane by providing accessory proteins that are normally used to support Pdr5p overexpression. This facet of the present invention may have considerable advantage over other systems that give high level expression without providing the complementary network of molecules needed for successful high volume intracellular trafficking and functional integration of the heterologous membrane protein into the plasma membrane.

The inclusion of the sec6-4 mutation in the host AD1-8u$^-$ background adds a further dimension to the system by allowing new assays that can exploit the orientation and electrochemical properties of secretory vesicles. It may also allow the hyper-expression of a wide range of biologically, pharmaceutically, and agrochemically relevant plasma membrane proteins for which suitable whole cell and in vitro assays can be developed by those skilled in the art. This aspect is complemented by the construction of the pABC3 vector as part of this invention. The pABC3 vector is designed to simplify the directional cloning of large membrane proteins such as the ABC-type transporters, avoid the need to consider downstream termination sequences and allow ready excision of the linear transformation cassette. Other modifications of this vector that are envisaged include the provision of vector elements in cassette form to allow ease of replacement by alternative elements, the insertion of features such as his-tags and other markers that will facilitate protein purification and studies of subcellular localization, the development of constructs that will allow plasmid-based expression, and the modification or replacement of the PDR5 promoter region to allow inducible gene expression. A host strain, such as AD1-8u⁻, could also be modified to minimize background interference by deleting other host homologues of genes to be expressed from the PDR5 or other locus. A preferred host strain could also be modified to contain a conditionally active version of Pdr1-3p for the purposes of inducible expression from the PDR5 locus.

It will be appreciated that it is not intended to limit the invention to the above mentioned examples only, many variations being possible such as would readily occur to a person of skill in the art without departing from the scope of the invention as defined in the accompanying claims.

INDUSTRIAL APPLICABILITY

The present invention provides an in vitro cell based expression system which is useful for high throughput screening for compounds which may be agonists or antagonists of membrane proteins involved in multi-drug resistance.

REFERENCES

1 Albertson G. D., M. Niimi, R. D. Cannon, and H. F. Jenkinson. 1996. Multiple efflux mechanisms are involved in *Candida albicans* fluconazole resistance. Antimicrob. Agents Chemother. 40:2835-2841.
2 Balzi, E., M. Wang, S. Leterme, L. Van Dyck, and A. Goffeau. 1994. PDR5, a novel yeast multidrug resistance conferring transporter controlled by the transcription regulator PDR1. J. Biol. Chem. 269:2206-2214.
3 Belli G., E. Gari, M. Aldea, E. Herrero. 1998. promoter analysis of essential yeast genes using a promoter-substitution cassette and the tetracycline-regulatable dual expression system. Yeast 14: 1127-1138
4 Boeke, J. D., F. LaCroute, G. R. Fink G R. 1984 A positive selection for mutants lacking orotidine-5'-phosphate decarboxylase activity in yeast: 5-fluoro-orotic acid resistance. Mol Gen Genet. 197:345-6.
5 Bradford, M. M. 1976. A rapid and sensitive method for the quantitation of microgram quantities of protein utilizing the principle of protein-dye binding. Anal. Biochem. 72:248-254.
6 Cannon, R. D., K. Niimi, H. F. Jenkinson, and M. G. Shepherd. 1994. Molecular cloning and expression of the *Candida albicans* β-N-acetylglucosaminidase (HEX1) gene. J. Bacteriol. 176:2640-2647.
7 Carvajal, E., H. B. van-den-Hazel, A. Cybularz-Kolaczkowska, E. Balzi, and A. Goffeau. 1997. Molecular and phenotypic characterization of yeast PDR1 mutants that show hyperactive transcription of various ABC multidrug transporter genes. Mol. Gen. Genet. 256:406-415.
8 Clark, F. S., T. Parkinson, C. A. Hitchcock, and N. A. R. Gow. 1996. Correlation between rhodamine 123 accumulation and azole sensitivity in *Candida* species: Possible role for drug efflux in drug resistance. Antimicrob. Agents Chemother. 40:419-425.
9 Decottignies, A., and A. Goffeau. 1997. Complete inventory of the yeast ABC proteins. Nature Genet. 15:137-145.
10 Decottignies, A., A. M. Grant, J. W. Nichols, H. de Wet, D. B. McIntosh, and A. Goffeau. 1998. ATPase and multidrug transport activities of the overexpressed yeast ABC protein Yor1p. J. Biol. Chem. 273:12612-12622.
11 Decottignies, A., M. Kolaczkowski, E. Balzi, and A. Goffeau. 1994. Solubilization and characterization of the overexpressed PDR5 multidrug resistance nucleotide triphosphatase of yeast. J. Biol. Chem. 269:12797-12803.
12 Fling, M. E., J. Knopf, A. Tamarkin, J. A. Gorman, H. A. Smith and Y. Koltin 1991. Analysis of a *Candida albicans* gene that encodes a novel mechanism for resistance to benomyl and methotrexate. Mol. Gen. Genet. 227:318-329.
13 Goffeau, A., and J-P. Dufour. 1988. Plasma membrane ATPase from the yeast *Saccharomyces cerevisiae*. Meth. Enzymol. 157:528-533.
14 Huang P., K. Stroffekova, J. Cuppoletti, S. K. Mahanty. and G. A. Scarborough. 1996. Functional expression of the cystic fibrosis transmembrane conductance regulator in yeast. Biochim. Biophys. Acta 1281:80-90.
15 de Kerchove d'Exaerde A., P. Supply, J. P Dufour, P. Bogaerts, D. Thines, A. Goffeau and M. Boutry. 1995. Functional complementation of a null mutation of the yeast *Saccharomyces cerevisiae* plasma membrane H⁺-ATPase by a plant H⁺-ATPase gene. J. Biol. Chem. 270:23828-23837.
16 Kolaczkowski, M., M. van der Rest, A. Cybularz-Kolaczkowska, J. P. Soumillion, W. N. Konings, and A. Goffeau. 1996. Anticancer drugs, ionophoric peptides, and steroids as substrates of yeast multidrug transporter Pdr5p. J. Biol. Chem. 271:31543-31548.
17 Krishnamurthy, S., U. Chatterjee, V. Gupta, R. Prasad, P. Das, P. Snehlata, S. E. Hasnain, and R. Prasad. 1998. Deletion of transmembrane domain 12 of CDR1, a multidrug transporter from *Candida albicans*, leads to altered drug specificity: Expression of a yeast multidrug transporter in baculovirus expression system. Yeast 14:535-550.
18 Krishnamurthy, S., V. Gupta, P. Snehlata, and R. Prasad. 1998. Characterisation of human steroid hormone transport mediated by Cdr1p, a multidrug transporter of *Candida albicans*, belonging to the ATP binding cassette super family. FEMS Microbiol. Lett. 158:69-74.
19 Luo H., P. Morsomme and M. Boutry. 1999. The two major types of plant plasma membrane H⁺-ATPases show differential enzymatic properties and confer differential pH sensitivity on yeast growth. Plant Physiology 119:627-624.
Maesaki, S., P. Marichal, H. Vanden Bossche, D. Sanglard, and S. Kohno. 1999. Rhodamine 6G efflux for the detection of CDR1-overexpressing azole-resistant *Candida albicans* strains. J. Antimicrob. Chemother. 44:27-31.
21 Mahanty S. K., U. S. Rao, R. A. Nicholas and G. A. Scarborough. 1994. High yield expression of the *Neurospora crassa* plasma membrane H⁺-ATPase in *Saccharomyces cerevisiae*. J. Biol. Chem 269:17705-17712.
22 Mao Q. and G. A. Scarborough. 1997. Purification of functional P-glycoprotein expressed in *Saccharomyces cerevisiae*. Biochim. Biophys. Acta 1327:107-118.
23 Marchetti, O., J. M. Entenza, D. Sanglard, J. Bille, M. P. Glauser, and P. Moreillon. 2000. Fluconazole plus cyclosporine: a fungicidal combination effective against experimental endocarditis due to *Candida albicans*. Antimicrob. Agents Chemother. 44:2932-2938.
24 Marchetti, O., P. Moreillon, M. P. Glauser, J. Bille, and D. Sanglard. 2000a. Potent synergism of the combination of fluconazole and cyclosporine in *Candida albicans*. Antimicrob. Agents Chemother. 44:2373-2381.

25 Mitchell, D. J., D. T. Kim, L. Steinman, C. G. Fathman and J. B. Rothbard, 2000. Polyargine enters cells more efficiently than other polycationic homopolymers. J. Pepeide Res. 56: 318-325

26 Miyazaki, H., Y. Miyazaki, A. Geber, T. Parkinson, C. Hitchcock, D. J. Falconer, D. Ward, D. ward, K. Marsden, J. E. Bennet (1998) Fluconazole resistance associated with drug efflux and increased transcription of a drug transporter gene, PDH1, in Candida glabrata. Antimicrob. Agents Chemother. 42: 1695-1701.

27 Monk, B. C., M. B. Kurtz, J. A. Marrinan, and D. S. Perlin. 1991. Cloning and characterization of the plasma membrane $H^+$-ATPase from Candida albicans. J. Bacteriol. 173:6826-6836.

28 Nakayama, H., M. Izuta, S. Shigehisa, E. Y. Sihta, Y. Sato, T. Yamazaki, M. Arisawa, K. Kitada. 1998. A controllable gene-expression system for the pathogenic fungus Candida glabrata. 144:2407-2415.

29 Potenza, M., R. Bowser, H. Muller, P. Novick. 1992 SEC6 encodes an 85 kDa soluble protein required for exocytosis in yeast. Yeast. 8:549-58.

30 Prasad, R., P. De Wergifosse, A. Goffeau, and E. Balzi. 1995. Molecular cloning and characterization of a novel gene of Candida albicans, CDR1, conferring multiple resistance to drugs and antifungals. Curr. Genet. 27:320-329.

31 Sambrook, J., E. F. Fritsch, and T. Maniatis. 1989. Molecular cloning: a laboratory manual, 2nd ed. Cold Spring Harbor Press, Cold Spring Harbor, N.Y.

32 Sanglard, D., F. Ischer, M. Monod and J. Billie. 1996. Susceptibilities of Candida albicans multidrug transporter mutants to various antifungal agents and metabolic inhibitors. Antimicrob. Agents Chemother. 40:2300-2305

33 Sanglard D., F. Ischer, M. Monod and J. Billie. 1997 Cloning of Candida albicans genes conferring resistance to azole antifungal agents: characterization of CDR2, a new multidrug ABC transporter. Microbiol. 143:404-416.

34 Sanglard D., K. Kuchler, F. Ischer, M. Monod and J. Billie. 1995. Mechanisms of resistance to azole antifungal agents in Candida albicans isolates from AIDS patients involve specific multidrug transporters. Antimicrob. Agents Chemother. 39:2378-2386.

35 Scherer, S., and D. A. Stevens. 1987. Application of DNA typing methods to epidemiology and taxonomy of Candida species. J. Clin. Microbiol. 25:675-679.

36 Seto-Young, D., S, Na, B. C. Monk, J. E. Haber, and D. S. Perlin. 1994. Mutational analysis of the first extracellular loop region of the $H^+$-ATPase from Saccharomyces cerevisiae. J. Biol. Chem. 269:23988-23995

37 Schwartz A., K. Whitmer, G. Grupp, L. Grupp, R. J. Adams and S.-W. Lee. 1982. Mechanism of action of digitalis; is the $Na^+$, $K^+$-ATPase the pharmacological receptor? Ann. N.Y. Acad. Sci. 402:253-271.

38 White, T C. 1997. Increased mRNA levels of ERG16, CDR and MDR1 correlate with increases in azole resistance in Candida albicans isolates from a patient infected with Human Immunodeficiency Virus. Antimicrob. Agents Chemother. 41:1482-1487.

39 White, T. C., K. A. Marr, R. A. Bowden. 1998 Clinical, cellular and molecular factors that contribute to antifungal resistance. Clin. Microbiol. Reviews. 11:382-402.

40 Wilson, R. B., D. Davis, B. M Enloe, A. P. Mitchell. 2000 A recyclable Candida albicans URA3 cassette for PCR product-directed gene disruptions. Yeast. 16:65-70.

What we claim is:

1. A protein expression system comprising:
   i) a host yeast cell comprising a mutant strain deficient in one or more naturally occurring drug efflux pump proteins; and
   ii) a plasmid vector pABC3 containing the coding sequence for a target heterologous membrane protein, said sequence being under the control of a PDR5 promoter.

2. A protein expression system as claimed in claim 1, wherein the host cell is a yeast cell of the genus *Saccharoimyces*.

3. A protein expression system as claimed in claim 1, wherein the host cell is the *Saccharomyces cerevisiae* AD1-8u⁻ strain.

4. The protein expression system as claimed in claim 1, wherein the host cell contains a mutation that leads to the formation of secretory vesicles whose ability to fuse with the plasma membrane is temperature sensitive.

5. The protein expression system as claimed in claim 4, wherein the host cell is a sec6-4 mutant of the AD1-8u⁻ strain.

6. The protein expression system as claimed in claim 1, wherein the coding sequence of the target heterologous membrane protein and PDR5 promoter are incorporated into the genome of the host cell.

7. A protein expression system as claimed in claim 1, wherein the coding sequence comprises the entire natural coding sequence of the target heterologous membrane protein.

8. The protein expression system as claimed in claim 6, wherein the target heterologous membrane protein is a drug efflux pump protein selected from the group consisting of pump proteins involved in multidrug resistance in fungi, P-glycoprotein, and cystic fibrosis transmembrane conductance regulator.

9. The protein expression system as claimed in claim 1, wherein the target heterologous membrane protein is a drug efflux pump protein.

10. The protein expression system as claimed in claim 9, where the target heterologous membrane protein is selected from the group consisting of *Candida albicans* Cdr1p, *Candida albicans* Cdr2p, *Candida galbrata* Cdr1p and *Candida albicans* Pdh1p.

11. A protein expression system as claimed in claim 1 wherein the target heterologous membrane protein is of a different class to the class of one or more naturally occurring drug efflux pump proteins which have been deleted from the host cell.

12. The protein expression system as claimed in claim 11 wherein the target heterologous membrane protein is selected from the *Candida albicans* Ben$^R$P and Erg11p.

13. The protein expression system as claimed in claim 6, wherein the host cell is *Saccharomyces cerevisiae*, and wherein the PDR5 promoter is under the control of a transcriptional regulator so as to induce over-expression of the target heterologous membrane protein coding sequence in the membrane of the host cell.

14. The protein expression system as claimed in claim 13, wherein the transcriptional regulator is the Pdr1-3p transcriptional regulator.

15. A method of screening compounds to identify pharmaceuticals or agrochemicals comprising the steps of:
   i) transforming the chromosomal DNA of a host yeast cell with DNA comprising a mutant strain deficient in one or more naturally occurring drug efflux pump proteins, with a vector, pABC3 containing a coding sequence for a target heterologous membrane efflux pump protein, said sequence being under the control of a PDR5 promoter;
   ii) introducing at least one candidate compound to said host cell environment or the environment of a plasma membrane fraction derived from the transformed host strain; and
   iii) measuring the effect, if any, of the candidate compound on the host cell growth and/or viability and/or specific biochemical or physiological functions mediated by the target membrane protein; and/or measuring the binding of the candidate compound to the target cell membrane protein.

16. The method as claimed in claim 15, wherein the host cell is a yeast cell of the genus *Saccharomyces*.

17. The method as claimed in claim 16, wherein the host cell is the *Saccharomyces cerevisiae* AD1-8u⁻ strain.

18. The method as claimed in claim 17, wherein the host cell is a sec6-4 mutant of the AD1-8u strain.

19. The method as claimed in claim 15, wherein the drug efflux drug pump protein is selected from the group consisting of pump proteins involved in multidrug resistance in fungi, the P-glycoprotein, and the cystic fibrosis transmembrane conductance regulator.

20. The method as claimed in claim 15, wherein the candidate compound is an efflux pump inhibitor.

21. The method as claimed in claim 15, wherein the host cell comprises a Pdr1-3p transcriptional regulator.

22. A plasmid vector pABC3.

23. A kit for screening for drugs useful as a pharmaceutical or agrochemical comprising:
   (i) a host yeast cell comprising mutant strain deficient in one or more naturally occurring drug efflux pump proteins;
   (ii) a plasmid vector, pABC3; and
   (iii) instructions to carry out insertion of a coding sequence of a target heterologous membrane protein into said pABC3 plasmid vector, said transformation, and drug screening procedures.

24. The kit as claimed in claim 23 wherein said host cell comprises *S. cerevisiae* AD1-8u⁻ and coding sequence of a heterologous drug efflux pump protein under the control of a PDR5 promoter.

25. The kit as claimed in claim 23, wherein said drug efflux pump protein is selected from the group comprising *C albicans* Cdr1p, Cdr2p, Ber$^R$p, Erg11p, and *C. galbrata* Cdr1p and Pdh1p.

\* \* \* \* \*

```
                         SEQUENCE LISTING

<160> NUMBER OF SEQ ID NOS: 17

<210> SEQ ID NO 1
<211> LENGTH: 30
<212> TYPE: DNA
<213> ORGANISM: Artificial Sequence
<220> FEATURE:
<223> OTHER INFORMATION: Description of Artificial Sequence: Made in Lab

<400> SEQUENCE: 1
ctttaaaagg tcaactagta aaaaattatg                                        30

<210> SEQ ID NO 2
<211> LENGTH: 27
<212> TYPE: DNA
<213> ORGANISM: Artificial Sequence
<220> FEATURE:
<223> OTHER INFORMATION: Description of Artificial Sequence: Made in Lab

<400> SEQUENCE: 2
caataataca ctagtttgca acggaag                                           27

<210> SEQ ID NO 3
<211> LENGTH: 79
<212> TYPE: DNA
<213> ORGANISM: Artificial Sequence
<220> FEATURE:
<223> OTHER INFORMATION: Description of Artificial Sequence: Made in Lab

<400> SEQUENCE: 3
tcccgtctag ttaatcactc ggaaggaaac aacgagtgag gtttcgtgtc attctctaga       60
ttttcccagt cacgacgtt                                                    79
```

<210> SEQ ID NO 4
<211> LENGTH: 80
<212> TYPE: DNA
<213> ORGANISM: Artificial Sequence
<220> FEATURE:
<223> OTHER INFORMATION: Description of Artificial Sequence: Made in Lab

<400> SEQUENCE: 4
tgctaccaag ctaacaaaag gatcaggctg cccaaacgga cgtagactca ctgggctccg    60
tgtggaattg tgagcggata                                                80

<210> SEQ ID NO 5
<211> LENGTH: 20
<212> TYPE: DNA
<213> ORGANISM: Artificial Sequence
<220> FEATURE:
<223> OTHER INFORMATION: Description of Artificial Sequence: Made in Lab

<400> SEQUENCE: 5
tccagagagt ataactcctg                                                20

<210> SEQ ID NO 6
<211> LENGTH: 20
<212> TYPE: DNA
<213> ORGANISM: Artificial Sequence
<220> FEATURE:
<223> OTHER INFORMATION: Description of Artificial Sequence: Made in Lab

<400> SEQUENCE: 6
tgttggaaat ttctcccgtg                                                20

<210> SEQ ID NO 7
<211> LENGTH: 22
<212> TYPE: DNA
<213> ORGANISM: Artificial Sequence
<220> FEATURE:
<223> OTHER INFORMATION: Description of Artificial Sequence: Made in Lab

<400> SEQUENCE: 7
aatgcaggag ttttacagtg gc                                             22

<210> SEQ ID NO 8
<211> LENGTH: 46
<212> TYPE: DNA
<213> ORGANISM: Artificial Sequence
<220> FEATURE:
<223> OTHER INFORMATION: Description of Artificial Sequence: Made in Lab

<400> SEQUENCE: 8
gtcaaaatta attaaaaaat gtcagattct aagatgtcgt cgcaag                   46

<210> SEQ ID NO 9
<211> LENGTH: 60
<212> TYPE: DNA
<213> ORGANISM: Artificial Sequence
<220> FEATURE:
<223> OTHER INFORMATION: Description of Artificial Sequence: Made in Lab

<400> SEQUENCE: 9
cacgcggccg cttagtgatg gtgatggtga tgtttcttat ttttttctc tctgttaccc     60

<210> SEQ ID NO 10
<211> LENGTH: 35
<212> TYPE: DNA
<213> ORGANISM: Artificial Sequence
<220> FEATURE:
<223> OTHER INFORMATION: Description of Artificial Sequence: Made in Lab -continued

<400> SEQUENCE: 10
catctactta cattaattaa cacaatgcat tacag					35

<210> SEQ ID NO 11
<211> LENGTH: 30
<212> TYPE: DNA
<213> ORGANISM: Artificial Sequence
<220> FEATURE:
<223> OTHER INFORMATION: Description of Artificial Sequence: Made in Lab

<400> SEQUENCE: 11
ggaaaacaat gcggccgcct aattagcata					30

<210> SEQ ID NO 12
<211> LENGTH: 41
<212> TYPE: DNA
<213> ORGANISM: Artificial Sequence
<220> FEATURE:
<223> OTHER INFORMATION: Description of Artificial Sequence: Made in Lab

<400> SEQUENCE: 12
ttcaagaaga ttaattaaca atatggctat tgttgaaact g					41

<210> SEQ ID NO 13
<211> LENGTH: 42
<212> TYPE: DNA
<213> ORGANISM: Artificial Sequence
<220> FEATURE:
<223> OTHER INFORMATION: Description of Artificial Sequence: Made in Lab

<400> SEQUENCE: 13
gaatcgaaag aaagcggccg ctttattaaa acatacaagt tt					42

<210> SEQ ID NO 14
<211> LENGTH: 49
<212> TYPE: DNA
<213> ORGANISM: Artificial Sequence
<220> FEATURE:
<223> OTHER INFORMATION: Description of Artificial Sequence: Made in Lab

<400> SEQUENCE: 14
gttttcgtgg ccgctcgggc caaagactta attaaaaaat gcccgaggc					49

<210> SEQ ID NO 15
<211> LENGTH: 32
<212> TYPE: DNA
<213> ORGANISM: Artificial Sequence
<220> FEATURE:
<223> OTHER INFORMATION: Description of Artificial Sequence: Made in Lab

<400> SEQUENCE: 15
acccacatat agcggccgca tatgagaaga cg					32

<210> SEQ ID NO 16
<211> LENGTH: 19
<212> TYPE: DNA
<213> ORGANISM: Artificial Sequence
<220> FEATURE:
<223> OTHER INFORMATION: Description of Artificial Sequence: Made in Lab

<400> SEQUENCE: 16
atcacgattc agcaccttt					19

```
<210> SEQ ID NO 17
<211> LENGTH: 20
<212> TYPE: DNA
<213> ORGANISM: Artificial Sequence
<220> FEATURE:
<223> OTHER INFORMATION: Description of Artificial Sequence: Made in Lab

<400> SEQUENCE: 17
cccaaaattt ggcattgaaa                                              20
```